United States Patent [19]

Zon et al.

[11] Patent Number: 5,700,927
[45] Date of Patent: Dec. 23, 1997

[54] TBC1 GENE AND USES THEREOF

[75] Inventors: Leonard Zon, Wellesley; Paul Richardson, Boston, both of Mass.

[73] Assignee: The Children's Medical Center Corporation, Boston, Mass.

[21] Appl. No.: 363,300

[22] Filed: Dec. 23, 1994

[51] Int. Cl.$^6$ .......................... C12N 15/12; C07K 14/475
[52] U.S. Cl. ........................................... 536/23.5; 530/350
[58] Field of Search ........................... 536/23.5; 530/350

[56] References Cited

U.S. PATENT DOCUMENTS 5,302,706  4/1994  Smith, Jr. ........................... 536/23.1

OTHER PUBLICATIONS

Ackerman, S.J., et al., "Expression of Gata–Binding Proteins in Human Eosinophils and Basophils: Potential Role in Gene Transcription"; *The Faseb Journal*, A1435:2893 (1992).

Bennett, J.M., et al., "Proposals for the classification of the myelodysplastic syndrome"; *British Journal of Hermatology*, 51:189–199, (1982).

Castaigne, S., et al., "All–Trans Retinoic Acid as a Differentiation Therapy for Acute Promyelocytic Leukeimia. I. Clinical Results"; *Blood* 76:1704–1709 (1990).

Castaigne, S., et al., "Does Treatment with ARA–C in Low Dosage Cause Differentiation of Leukemic Cells?"; *Blood* 62:85–86 (1983).

Desforges, Jane F., "Cytarabine: Low–Dose, High–Dose, No Dose?"; *The New England Journal of Medicine*, 309:1637–1638 (1983).

Fialkow, P.J., et al., "Evidence that Essential Thrombocythemia is a Clonal Disorder With Origin in a Multipotent Stem Cell"; *Blood* 58:916–919 (1981).

Fialkow, P.J., et al., "Expression in Cells Restricted to Granulocytic and Monocytic Differentiation"; *The New England Jouranl of Medicine*, 301:1–5 (1979).

Grier, H.E., et al., "Chronic Myeloproliferative Disorders"; *Acute and Chronic Myeloproliferative Disorders and Myelodysplasia*, 36:1288–1318.

Meng–er, H. et al., "Use of All–Trans Retinoic Acid in Treatment of Acute Promyelocytic Leukemia"; *Blood*, 72:567–572 (1988).

Mouthon, M. et al., "Expression of tal–1 and GATA–Binding Proteins During Human Hematopoiesis"; *Blood* 81:647–655 (1993).

Pevny, L., et al., "Erthroid differentiation in chimaeric mice blocked by a targted mutation in the gene for transcription factor GATA–1"; *Nature* 349:257–349 (1991).

Richardson, P. et al., "Cloning of Potential Targest of GATA–1 Activation During Mast Cell Development"; *Journal of Cellular Biochemistry*, B679:170 (1993).

Schrier, Stanley L., "VIII The Leukemias and the Myeloproliferative Disorders"; *HEMA* 5:1–28 (1989).

Tsai, S.F., "Functional analysis and in vivo footprinting implicate the erythroid transcription factor GATA–1 as a positive regulator of its own promoter"; *Genes & Development*, 5:919–931 (1991).

Visvader, J. et al., "Megakaryocytic Differentiation Induced in 416B Myeloid Cells by GATA–2 and GATA–3 Transgenes or 5–Azacytidine is Tightly Coupled to GATA–1 Expression"; *Blood*, 82:1493–1501 (1993).

Visvader, J.E. et al., "GATA–1 but not SCL induces megakaryocytic differentiation in an early myeloid line"; *The EMBO Journal*, 11:4557–4564 (1992).

Wisch, J. S. et al., "Response of Preleukemic Syndromes to Continuous Infusion of Low–Dose Cytarabine"; The New England Journal of Medicine, 309:1599–1602 (1983).

Zon, L. et al., "GATA–binding Transcription Factors in Mast Cells Regulate the Promoter of the Mast Cell Carboxypeptidase A Gene"; *The Journal of Biological Chemistry*, 266:22948–22953 (1991).

*Primary Examiner*—Stephen Walsh
*Assistant Examiner*—Daryl A. Basham
*Attorney, Agent, or Firm*—Fish & Richardson P.C.

[57] ABSTRACT

Disclosed is a substantially pure DNA encoding a Tbc1 polypeptide; a substantially pure Tbc1 polypeptide; and methods of using such DNA to express Tbc1 in leukemic stem cells and treat certain leukemias. Also disclosed are methods for diagnosing other leukemias and spermatogenesis disorders by assaying for Tbc1 expression.

3 Claims, 7 Drawing Sheets

```
   1 ACCTCGGACCGACCGTCTCTTCAACCCGCAAGAGAAGCAGAGACTGTGGAGTGGACCCCC    60
  61 ACCCCAGCAGCGTGGGGCGGCAAGAGCACAGCCAGCTGAGGACCATGGACGCCCCGCCCG   120
 121 CCCAGGCCATCTTCTGGGTGCCCGGGAGCACCTGCGCGCCCTAGCTCAGCGCGGAGTTCT   180
 181 GAGCGTGCCACCTCACTGGATTCTGCCCTCAGAAGCACGTGAAATAGATCACTTCATTTA   240
 241 AAGTAGGAAAATAGTAGCACGTTTTTACCGGCTCTCCAGACCTCTCCCAGGATGGAGGCA   300
 301 ATCACATTCACAGCGAGGAAGCATCCGTTTCCCTAACGAAGTCTCCGTGGACTTCGGCTT   360
 361 GCAGCTGGTTGGGTCTCCTTACCCGTGCATTCTCTCACCACTATGCCCATGCTGCCGTGG   420
                                        M   P   M   L   P   W
 421 GTGGTAGCCGAGGTACGAAGACTCAGTGGCCAGTGCTCTAAAAAGGAGCCTAGGACAAAG   480
      V   V   A   E   V   R   R   L   S   G   Q   C   S   K   K   E   P   R   T   K
 481 CAAGTCCGCCTTTGGGTTTCGCCCTCCGGACTGCGGTGCGAGCCTGACCTGGAGAAAAGT   540
      Q   V   R   L   W   V   S   P   S   G   L   R   C   E   P   D   L   E   K   S
 541 CAACCATGGGACCCGCTCATCTGTTCCAGCATCTTTGAGTGCAAGCCTCAGCGTGTGCAC   600
      Q   P   W   D   P   L   I   C   S   S   I   F   E   C   K   P   Q   R   V   H
 601 AAACTGATTCACAACAGTCACGACCCGAGCTACTTTGCTTGCCTCATTAAGGAGGATGCT   660
      K   L   I   H   N   S   H   D   P   S   Y   F   A   C   L   I   K   E   D   A
 661 GCGCACAGGCAGAGCCTCTGCTATGTGTTTAAAGCAGACGATCAAACAAAAGTGCCTGAG   720
      A   H   R   Q   S   L   C   Y   V   F   K   A   D   D   Q   T   K   V   P   E
 721 ATCATCAGCTCCATCCGGCAGGCCGGGAAGATTGCCCGCCAGGAAGAGCTGCGTTGCCCC   780
      I   I   S   S   I   R   Q   A   G   K   I   A   R   Q   E   E   L   R   C   P
 781 TCCGAGTTCGACGATACCTTCGCCAAAAAGTTCGAGGTGCTCTTCTGTGGCCGGGTGACT   840
      S   E   F   D   D   T   F   A   K   K   F   E   V   L   F   C   G   R   V   T
 841 GTGGCTCACAAGAAGGCCCCACCCGCACTGATTGACGAGTGTATCGAGAAGTTCAACCAT   900
      V   A   H   K   K   A   P   P   A   L   I   D   E   C   I   E   K   F   N   H
 901 GTGAGCTGTGGTCGCAGAACGGACTGGGAAGCGCCCACCGGGCAGCCATCAGCGCCTGGC   960
      V   S   C   G   R   R   T   D   W   E   A   P   T   G   Q   P   S   A   P   G
 961 CCCAGGCCCATGCGCAAATCCTTCTCACAGCCTGGACTGCGCTCGCTGGCCTTCAGGAAG  1020
      P   R   P   M   R   K   S   F   S   Q   P   G   L   R   S   L   A   F   R   K
1021 GAGTTCCAGGACGCTAGCCTCCGCAGTAGCACCTTTAGCTCCTTTGACAATGACATAGAG  1080
      E   F   Q   D   A   S   L   R   S   S   T   F   S   S   F   D   N   D   I   E
1081 AACCACCTCATCGGTGGGCACAATGTGGTTCAGCCCACAGACATGGAGGAGAACCGAACT  1140
      N   H   L   I   G   G   H   N   V   V   Q   P   T   D   M   E   E   N   R   T
1141 ATGCTGTTCACGATTGGCCCATCTGAAGTTTACCTCATCAGTCCTGACACCAAAAAGATT  1200
      M   L   F   T   I   G   P   S   E   V   Y   L   I   S   P   D   T   K   K   I
1201 GCACTGGAGAAAAATTTTAAGGAGATATCCTTTTGCTCTCAGGGCATCAGACATGTGGAC  1260
      A   L   E   K   N   F   K   E   I   S   F   C   S   Q   G   I   R   H   V   D
1261 CACTTTGGATTCATCTGCCGAGAGTGCTCGGGTGGCGGCAGTGGCGGCTTTCATTTTGTC  1320
      H   F   G   F   I   C   R   E   C   S   G   G   G   S   G   G   F   H   F   V
1321 TGTTACGTGTTCCAGTGCACAAATGAAGCTCTGGTTGACGAGATCATGATGACTCTGAAG  1380
      C   Y   V   F   Q   C   T   N   E   A   L   V   D   E   I   M   M   T   L   K
1381 CAGGCTTTCACGGTAGCTGCGGTGCAGCAGACGGCTAAGGCACCAGCCCAGCTCTGTGAG  1440
      Q   A   F   T   V   A   A   V   Q   Q   T   A   K   A   P   A   Q   L   C   E
1441 GGCTGCCCCTTGCAAGGCCTGCACAAGCTCTGCGAAAGGATAGAGGGAATGAATTCATCT  1500
      G   C   P   L   Q   G   L   H   K   L   C   E   R   I   E   G   M   N   S   S
1501 AAAACCAAATTAGAACTCCAGAAGCACTTGACCACACTGACCAATCAGGAGCAGGCCACC  1560
      K   T   K   L   E   L   Q   K   H   L   T   T   L   T   N   Q   E   Q   A   T
1561 ATATTCGAGGAGGTTCAGAAATTGAGACCAAGAAACGAGCAGCGAGAGAATGAATTAATT  1620
      I   F   E   E   V   Q   K   L   R   P   R   N   E   Q   R   E   N   E   L   I
1621 ATTTCTTTTCTGAGGTGCTTATATGAAGAGAAGCAAAAAGAGCACAGCCACACTGGGGCG  1680
      I   S   F   L   R   C   L   Y   E   E   K   Q   K   E   H   S   H   T   G   A
1681 CCAAAGCAGACACTACAGGTGGCAGCAGAGAATATTGGGAGTGACCTGCCACCCAGTGCT  1740
      P   K   Q   T   L   Q   V   A   A   E   N   I   G   S   D   L   P   P   S   A
1741 AGCCGGTTCAGGTTAGATTCGCTGAAGAACAGAGCAAAGAGGTCCTTAACAGAGTCCCTA  1800
      S   R   F   R   L   D   S   L   K   N   R   A   K   R   S   L   T   E   S   L
1801 GAGAGCATTCTGTCCCGGGGTAATAAAGCCAGAGGCCTGCAGGACCATTCCGCCAGTGTG  1860
      E   S   I   L   S   R   G   N   K   A   R   G   L   Q   D   H   S   A   S   V
1861 GATCTGGACAGCTCCACTTCTAGTACTCTAAGTAACACCAGCAAAGAGCTGTCCATGGGT  1920
      D   L   D   S   S   T   S   S   T   L   S   N   T   S   K   E   L   S   M   G
1921 GACAAGGAGGCCTTCCCCGTCTCTGAGACCTCCTTCAAGCTCCTTGGCTCCTCAGATGAC  1980
      D   K   E   A   F   P   V   S   E   T   S   F   K   L   L   G   S   S   D   D
1981 CTGTCCAGTGACTCAGAGGGCCACATTGCAGAAGAGTCTGCCCTGTTGTCACCCCAGCAG  2040
      L   S   S   D   S   E   G   H   I   A   E   E   S   A   L   L   S   P   Q   Q
2041 GCGTTCAGAAGGAGAGCCAACACCCTGAGTCATTTCCCAGTAGAGTGCCCTGCGCCTCCA  2100
      A   F   R   R   R   A   N   T   L   S   H   F   P   V   E   C   P   A   P   P
```

FIG. 1A

```
2101 GAACCTGCCCAGAGCTCTCCAGGGGTCTCTCAAAGGAAACTCATGCGGTACCACTCCGTG 2160
      E  P  A  Q  S  S  P  G  V  S  Q  R  K  L  M  R  Y  H  S  V
2161 AGCACAGAGACGCCTCATGAACGCAAGGACTTTGAATCCAAAGCAAACCACCTGGGTGAC 2220
      S  T  E  T  P  H  E  R  K  D  F  E  S  K  A  N  H  L  G  D
2221 ACAGATGGGACCCCCGTGAAGACCCGGCGGCACTCGTGGAGACAGCAGATATTCCTTCGA 2280
      T  D  G  T  P  V  K  T  R  R  H  S  W  R  Q  Q  I  F  L  R
2281 GTGGCCACTCCACAGAAGGCTTGTGACTCCCCGAGCAGATATGAAGATTATTCCGAGCTG 2340
      V  A  T  P  Q  K  A  C  D  S  P  S  R  Y  E  D  Y  S  E  L
2341 GGAGAGCTCCCTCCACGCTCCCCTTTAGAACCGGTGTGTGAGGACGGCCCATTTGGCCAG 2400
      G  E  L  P  P  R  S  P  L  E  P  V  C  E  D  G  P  F  G  Q
2401 TACAGGAAGAAAAGAGGAAGACGTCACGCGAGCTTCGAGAGCTGTGGAAAAAGGCCATCT 2460
      Y  R  K  K  R  G  R  R  H  A  S  F  E  S  C  G  K  R  P  S
2461 TGCAGCAGATCCTGCCTCGTCAGGATGGAGAAGGAGAATCAGAAGCTACAAGCCTCTGAA 2520
      C  S  R  S  C  L  V  R  M  E  K  E  N  Q  K  L  Q  A  S  E
2521 AACGATTTGCTGAACAAACGCCTCAAGCTTGACTATGAAGAAATCACTCCGTGTCTTAAA 2580
      N  D  L  L  N  K  R  L  K  L  D  Y  E  E  I  T  P  C  L  K
2581 GAAGTCACTACAGTGTGGGAAAAGATGCTTAGCACTCCAGGAAGATCCAAAATTAAGTTT 2640
      E  V  T  T  V  W  E  K  M  L  S  T  P  G  R  S  K  I  K  F
2641 GACATGGAAAAAGTGCACTCAGCTGTTGGGCAAGGTGTGCCACGTCATCACCGAGGTGAG 2700
      D  M  E  K  V  H  S  A  V  G  Q  G  V  P  R  H  H  R  G  E
2701 ATCTGGAAATTTCTAGCTGAGCAGTTCCACCTTAAACACCCATTTCCTAGTAAACAGCAG 2760
      I  W  K  F  L  A  E  Q  F  H  L  K  H  P  F  P  S  K  Q  Q
2761 CCAAAGGACGTGCCCTACAAAGAGCTCCTGAAGAAGCTGACCTCGCAGCAGCACGCCATT 2820
      P  K  D  V  P  Y  K  E  L  L  K  K  L  T  S  Q  Q  H  A  I
2821 CTCATCGACCTCGGGCGAACCTTTCCAACACATCCATACTTCTCTGCCCAGCTTGGAGCA 2880
      L  I  D  L  G  R  T  F  P  T  H  P  Y  F  S  A  Q  L  G  A
2881 GGTCAGCTGTCACTTTACAACATTCTGAAGGCCTACTCGCTTCTGGACCAGGAGGTTGGA 2940
      G  Q  L  S  L  Y  N  I  L  K  A  Y  S  L  L  D  Q  E  V  G
2941 TACTGCCAAGGTCTCAGCTTTGTGGCAGGCATTTTGCTTCTTCACATGAGTGAGGAAGAG 3000
      Y  C  Q  G  L  S  F  V  A  G  I  L  L  L  H  M  S  E  E  E
3001 GCGTTCAAGATGCTCAAGTTCCTGATGTTTGACATGGGGCTGCGGAAACAGTATCGGCCA 3060
      A  F  K  M  L  K  F  L  M  F  D  M  G  L  R  K  Q  Y  R  P
3061 GACATGATTATTTTGCAGATCCAGATGTACCAGCTGTCACGGCTCCTCCACGATTACCAC 3120
      D  M  I  I  L  Q  I  Q  M  Y  Q  L  S  R  L  L  H  D  Y  H
3121 CGAGACCTCTACAACCACCTGGAAGAGCACGAGACTGGCCCCCCTACGTACGCGGCTCCC 3180
      R  D  L  Y  N  H  L  E  E  H  E  T  G  P  P  T  Y  A  A  P
3181 TGGTTTCTCACCGTGTTCGCCTCACAGTTCCCACTCGGCTTTGTAGCCAGAGTCTTTGAT 3240
      W  F  L  T  V  F  A  S  Q  F  P  L  G  F  V  A  R  V  F  D
3241 ATGATCTTCCTTCAGGGATCAGAGGTCATATTTAAAGTAGCTTTAAGTCTTTTGGGGAGC 3300
      M  I  F  L  Q  G  S  E  V  I  F  K  V  A  L  S  L  L  G  S
3301 CATAAGCCCTTGATTCTACAGCATGAGAACCTGGAAACCATCGTGGACTTCATAAAGAAC 3360
      H  K  P  L  I  L  Q  H  E  N  L  E  T  I  V  D  F  I  K  N
3361 ACACTCCCCAACCTGGGCCTGGTGCAGATGGAGAAGACCATCAGTCAGGTGTTTGAGATG 3420
      T  L  P  N  L  G  L  V  Q  M  E  K  T  I  S  Q  V  F  E  M
3421 GACATCGCCAAGCAGCTCCAGGCCTATGAGGTCGAGTACCACGTCGTCCAGGAGGAGCTT 3480
      D  I  A  K  Q  L  Q  A  Y  E  V  E  Y  H  V  V  Q  E  E  L
3481 ATTGAGTCCTCGCCTCTCAGTGACAACCAAAGAATGGAGAAATTGGAGAAAACCAACAGC 3540
      I  E  S  S  P  L  S  D  N  Q  R  M  E  K  L  E  K  T  N  S
3541 ACGTTGCGCAAACAGAACCTTGACCTCCTGGAACAGTTGCAGGTGGCAAATGCTAGGATC 3600
      T  L  R  K  Q  N  L  D  L  L  E  Q  L  Q  V  A  N  A  R  I
3601 CAAAGCCTTGAAGCCACGGTAGAGAAACTTCTTACCAGCGAGAGTAAGCTGAAGCAGCGT 3660
      Q  S  L  E  A  T  V  E  K  L  L  T  S  E  S  K  L  K  Q  R
3661 GCGCTGACCCTGGAGGTGGAGCGTCGCCCTGCTGCAGATGGTGGAGGAGCTGCGGAGGCA 3720
      A  L  T  L  E  V  R  R  P  A  A  D  G  G  A  A  E  A
3721 AAGCGCCCGGCCCAGCACTCCAGAGCCAGACTGCACCCAGCTGGAGCCCACAGGCGATTG 3780
      K  R  P  A  Q  H  S  R  A  R  L  H  P  A  G  A  H  R  R  L
3781 ACCGCTGCCAGAAGAGACTGTGCACCATTAACACTGTCCAAGCCTTAATCAAGAGAGATG 3840
      T  A  A  R  R  D  C  A  P  L  T  L  S  K  P  *
3841 GAAGTCAGAGGCAGAGAAGAGAGAACTTCTCAGGGAGGAAACTGGCTGACCAGCCTGCAG 3900
3901 ATCCTTTTGAGCTCAGAACTTGGATTGGAGGACAAAAGTCTCAGAGTTATTGTTGTTTT 3960
3961 TGGTTCTAATCCGTCCCCTTTCCAGTCCTGGTTGTTGTAGCTTTAGATGGCATGGACATG 4020
4021 AATAAATTACATTTATGGC                                           4039
```

FIG. 1B

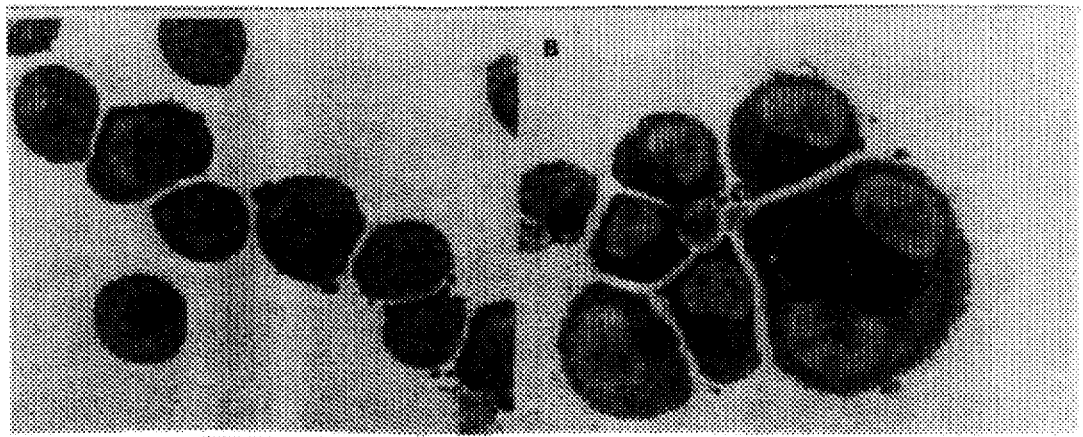
FIG. 2A  FIG. 2B
FIG. 2C  FIG. 2D
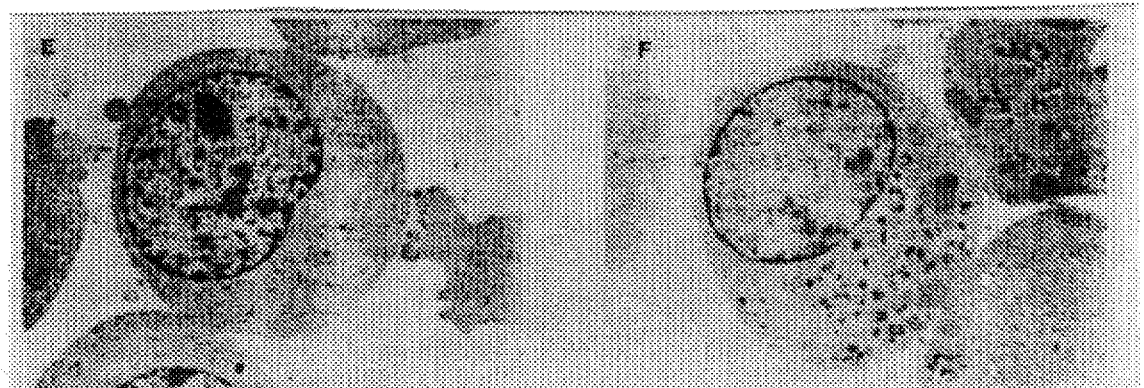
FIG. 2E  FIG. 2F

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 4039 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 403..3829

( x i ) SEQUENCE DESCRIPTION: SEQ ID NO:1:

```
ACCTCGGACC GACCGTCTCT TCAACCCGCA AGAGAAGCAG AGACTGTGGA GTGGACCCCC      60

ACCCCAGCAG CGTGGGGCGG CAAGAGCACA GCCAGCTGAG GACCATGGAC GCCCCGCCCG     120

CCCAGGCCAT CTTCTGGGTG CCCGGGAGCA CCTGCGCGCC CTAGCTCAGC GCGGAGTTCT     180

GAGCGTGCCA CCTCACTGGA TTCTGCCCTC AGAAGCACGT GAAATAGATC ACTTCATTTA     240

AAGTAGGAAA ATAGTAGCAC GTTTTTACCG GCTCTCCAGA CCTCTCCCAG GATGGAGGCA     300

ATCACATTCA CAGCGAGGAA GCATCCGTTT CCCTAACGAA GTCTCCGTGG ACTTCGGCTT     360

GCAGCTGGTT GGGTCTCCTT ACCCGTGCAT TCTCTCACCA   CT ATG CCC ATG CTG      414
                                                 Met Pro Met Leu
                                                  1

CCG TGG GTG GTA GCC GAG GTA CGA AGA CTC AGT GGC CAG TGC TCT AAA      462
Pro Trp Val Val Ala Glu Val Arg Arg Leu Ser Gly Gln Cys Ser Lys
 5              10                  15                  20

AAG GAG CCT AGG ACA AAG CAA GTC CGC CTT TGG GTT TCG CCC TCC GGA      510
Lys Glu Pro Arg Thr Lys Gln Val Arg Leu Trp Val Ser Pro Ser Gly
                25                  30                  35

CTG CGG TGC GAG CCT GAC CTG GAG AAA AGT CAA CCA TGG GAC CCG CTC      558
Leu Arg Cys Glu Pro Asp Leu Glu Lys Ser Gln Pro Trp Asp Pro Leu
        40                  45                  50

ATC TGT TCC AGC ATC TTT GAG TGC AAG CCT CAG CGT GTG CAC AAA CTG      606
Ile Cys Ser Ser Ile Phe Glu Cys Lys Pro Gln Arg Val His Lys Leu
            55                  60                  65

ATT CAC AAC AGT CAC GAC CCG AGC TAC TTT GCT TGC CTC ATT AAG GAG      654
Ile His Asn Ser His Asp Pro Ser Tyr Phe Ala Cys Leu Ile Lys Glu
 70                  75                  80

GAT GCT GCG CAC AGG CAG AGC CTC TGC TAT GTG TTT AAA GCA GAC GAT      702
Asp Ala Ala His Arg Gln Ser Leu Cys Tyr Val Phe Lys Ala Asp Asp
 85                  90                  95                 100

CAA ACA AAA GTG CCT GAG ATC ATC AGC TCC ATC CGG CAG GCC GGG AAG      750
Gln Thr Lys Val Pro Glu Ile Ile Ser Ser Ile Arg Gln Ala Gly Lys
                105                 110                 115

ATT GCC CGC CAG GAA GAG CTG CGT TGC CCC TCC GAG TTC GAC GAT ACC      798
Ile Ala Arg Gln Glu Glu Leu Arg Cys Pro Ser Glu Phe Asp Asp Thr
        120                 125                 130

TTC GCC AAA AAG TTC GAG GTG CTC TTC TGT GGC CGG GTG ACT GTG GCT      846
Phe Ala Lys Lys Phe Glu Val Leu Phe Cys Gly Arg Val Thr Val Ala
            135                 140                 145

CAC AAG AAG GCC CCA CCC GCA CTG ATT GAC GAG TGT ATC GAG AAG TTC      894
His Lys Lys Ala Pro Pro Ala Leu Ile Asp Glu Cys Ile Glu Lys Phe
 150                 155                 160
```

| | | | | | | | | | | | | | | | | |
|---|---|---|---|---|---|---|---|---|---|---|---|---|---|---|---|---|
| AAC | CAT | GTG | AGC | TGT | GGT | CGC | AGA | ACG | GAC | TGG | GAA | GCG | CCC | ACC | GGG | 942 |
| Asn | His | Val | Ser | Cys | Gly | Arg | Arg | Thr | Asp | Trp | Glu | Ala | Pro | Thr | Gly | |
| 165 | | | | 170 | | | | | | 175 | | | | | 180 | |
| CAG | CCA | TCA | GCG | CCT | GGC | CCC | AGG | CCC | ATG | CGC | AAA | TCC | TTC | TCA | CAG | 990 |
| Gln | Pro | Ser | Ala | Pro | Gly | Pro | Arg | Pro | Met | Arg | Lys | Ser | Phe | Ser | Gln | |
| | | | | 185 | | | | | 190 | | | | | 195 | | |
| CCT | GGA | CTG | CGC | TCG | CTG | GCC | TTC | AGG | AAG | GAG | TTC | CAG | GAC | GCT | AGC | 1038 |
| Pro | Gly | Leu | Arg | Ser | Leu | Ala | Phe | Arg | Lys | Glu | Phe | Gln | Asp | Ala | Ser | |
| | | | 200 | | | | | 205 | | | | | 210 | | | |
| CTC | CGC | AGT | AGC | ACC | TTT | AGC | TCC | TTT | GAC | AAT | GAC | ATA | GAG | AAC | CAC | 1086 |
| Leu | Arg | Ser | Ser | Thr | Phe | Ser | Ser | Phe | Asp | Asn | Asp | Ile | Glu | Asn | His | |
| | | 215 | | | | | 220 | | | | | 225 | | | | |
| CTC | ATC | GGT | GGG | CAC | AAT | GTG | GTT | CAG | CCC | ACA | GAC | ATG | GAG | GAG | AAC | 1134 |
| Leu | Ile | Gly | Gly | His | Asn | Val | Val | Gln | Pro | Thr | Asp | Met | Glu | Glu | Asn | |
| | 230 | | | | | 235 | | | | | 240 | | | | | |
| CGA | ACT | ATG | CTG | TTC | ACG | ATT | GGC | CCA | TCT | GAA | GTT | TAC | CTC | ATC | AGT | 1182 |
| Arg | Thr | Met | Leu | Phe | Thr | Ile | Gly | Pro | Ser | Glu | Val | Tyr | Leu | Ile | Ser | |
| 245 | | | | | 250 | | | | | 255 | | | | | 260 | |
| CCT | GAC | ACC | AAA | AAG | ATT | GCA | CTG | GAG | AAA | AAT | TTT | AAG | GAG | ATA | TCC | 1230 |
| Pro | Asp | Thr | Lys | Lys | Ile | Ala | Leu | Glu | Lys | Asn | Phe | Lys | Glu | Ile | Ser | |
| | | | | 265 | | | | | 270 | | | | | 275 | | |
| TTT | TGC | TCT | CAG | GGC | ATC | AGA | CAT | GTG | GAC | CAC | TTT | GGA | TTC | ATC | TGC | 1278 |
| Phe | Cys | Ser | Gln | Gly | Ile | Arg | His | Val | Asp | His | Phe | Gly | Phe | Ile | Cys | |
| | | | 280 | | | | | 285 | | | | | 290 | | | |
| CGA | GAG | TGC | TCG | GGT | GGC | GGC | AGT | GGC | GGC | TTT | CAT | TTT | GTC | TGT | TAC | 1326 |
| Arg | Glu | Cys | Ser | Gly | Gly | Gly | Ser | Gly | Gly | Phe | His | Phe | Val | Cys | Tyr | |
| | | 295 | | | | | 300 | | | | | 305 | | | | |
| GTG | TTC | CAG | TGC | ACA | AAT | GAA | GCT | CTG | GTT | GAC | GAG | ATC | ATG | ATG | ACT | 1374 |
| Val | Phe | Gln | Cys | Thr | Asn | Glu | Ala | Leu | Val | Asp | Glu | Ile | Met | Met | Thr | |
| | 310 | | | | | 315 | | | | | 320 | | | | | |
| CTG | AAG | CAG | GCT | TTC | ACG | GTA | GCT | GCG | GTG | CAG | CAG | ACG | GCT | AAG | GCA | 1422 |
| Leu | Lys | Gln | Ala | Phe | Thr | Val | Ala | Ala | Val | Gln | Gln | Thr | Ala | Lys | Ala | |
| 325 | | | | | 330 | | | | | 335 | | | | | 340 | |
| CCA | GCC | CAG | CTC | TGT | GAG | GGC | TGC | CCC | TTG | CAA | GGC | CTG | CAC | AAG | CTC | 1470 |
| Pro | Ala | Gln | Leu | Cys | Glu | Gly | Cys | Pro | Leu | Gln | Gly | Leu | His | Lys | Leu | |
| | | | | 345 | | | | | 350 | | | | | 355 | | |
| TGC | GAA | AGG | ATA | GAG | GGA | ATG | AAT | TCA | TCT | AAA | ACC | AAA | TTA | GAA | CTC | 1518 |
| Cys | Glu | Arg | Ile | Glu | Gly | Met | Asn | Ser | Ser | Lys | Thr | Lys | Leu | Glu | Leu | |
| | | | 360 | | | | | 365 | | | | | 370 | | | |
| CAG | AAG | CAC | TTG | ACC | ACA | CTG | ACC | AAT | CAG | GAG | CAG | GCC | ACC | ATA | TTC | 1566 |
| Gln | Lys | His | Leu | Thr | Thr | Leu | Thr | Asn | Gln | Glu | Gln | Ala | Thr | Ile | Phe | |
| | | 375 | | | | | 380 | | | | | 385 | | | | |
| GAG | GAG | GTT | CAG | AAA | TTG | AGA | CCA | AGA | AAC | GAG | CAG | CGA | GAG | AAT | GAA | 1614 |
| Glu | Glu | Val | Gln | Lys | Leu | Arg | Pro | Arg | Asn | Glu | Gln | Arg | Glu | Asn | Glu | |
| | 390 | | | | | 395 | | | | | 400 | | | | | |
| TTA | ATT | ATT | TCT | TTT | CTG | AGG | TGC | TTA | TAT | GAA | GAG | AAG | CAA | AAA | GAG | 1662 |
| Leu | Ile | Ile | Ser | Phe | Leu | Arg | Cys | Leu | Tyr | Glu | Glu | Lys | Gln | Lys | Glu | |
| 405 | | | | | 410 | | | | | 415 | | | | | 420 | |
| CAC | AGC | CAC | ACT | GGG | GCG | CCA | AAG | CAG | ACA | CTA | CAG | GTG | GCA | GCA | GAG | 1710 |
| His | Ser | His | Thr | Gly | Ala | Pro | Lys | Gln | Thr | Leu | Gln | Val | Ala | Ala | Glu | |
| | | | | 425 | | | | | 430 | | | | | 435 | | |
| AAT | ATT | GGG | AGT | GAC | CTG | CCA | CCC | AGT | GCT | AGC | CGG | TTC | AGG | TTA | GAT | 1758 |
| Asn | Ile | Gly | Ser | Asp | Leu | Pro | Pro | Ser | Ala | Ser | Arg | Phe | Arg | Leu | Asp | |
| | | | 440 | | | | | 445 | | | | | 450 | | | |
| TCG | CTG | AAG | AAC | AGA | GCA | AAG | AGG | TCC | TTA | ACA | GAG | TCC | CTA | GAG | AGC | 1806 |
| Ser | Leu | Lys | Asn | Arg | Ala | Lys | Arg | Ser | Leu | Thr | Glu | Ser | Leu | Glu | Ser | |
| | | 455 | | | | | 460 | | | | | 465 | | | | |
| ATT | CTG | TCC | CGG | GGT | AAT | AAA | GCC | AGA | GGC | CTG | CAG | GAC | CAT | TCC | GCC | 1854 |
| Ile | Leu | Ser | Arg | Gly | Asn | Lys | Ala | Arg | Gly | Leu | Gln | Asp | His | Ser | Ala | |
| | 470 | | | | | 475 | | | | | 480 | | | | | |

-continued

| | | | | | | | | | | | | | | | | |
|---|---|---|---|---|---|---|---|---|---|---|---|---|---|---|---|---|
| AGT | GTG | GAT | CTG | GAC | AGC | TCC | ACT | TCT | AGT | ACT | CTA | AGT | AAC | ACC | AGC | 1902 |
| Ser | Val | Asp | Leu | Asp | Ser | Ser | Thr | Ser | Ser | Thr | Leu | Ser | Asn | Thr | Ser | |
| 485 | | | | 490 | | | | | 495 | | | | | | 500 | |
| AAA | GAG | CTG | TCC | ATG | GGT | GAC | AAG | GAG | GCC | TTC | CCC | GTC | TCT | GAG | ACC | 1950 |
| Lys | Glu | Leu | Ser | Met | Gly | Asp | Lys | Glu | Ala | Phe | Pro | Val | Ser | Glu | Thr | |
| | | | | 505 | | | | 510 | | | | | 515 | | | |
| TCC | TTC | AAG | CTC | CTT | GGC | TCC | TCA | GAT | GAC | CTG | TCC | AGT | GAC | TCA | GAG | 1998 |
| Ser | Phe | Lys | Leu | Leu | Gly | Ser | Ser | Asp | Asp | Leu | Ser | Ser | Asp | Ser | Glu | |
| | | | 520 | | | | 525 | | | | 530 | | | | | |
| GGC | CAC | ATT | GCA | GAA | GAG | TCT | GCC | CTG | TTG | TCA | CCC | CAG | CAG | GCG | TTC | 2046 |
| Gly | His | Ile | Ala | Glu | Glu | Ser | Ala | Leu | Leu | Ser | Pro | Gln | Gln | Ala | Phe | |
| | | 535 | | | | 540 | | | | 545 | | | | | | |
| AGA | AGG | AGA | GCC | AAC | ACC | CTG | AGT | CAT | TTC | CCA | GTA | GAG | TGC | CCT | GCG | 2094 |
| Arg | Arg | Arg | Ala | Asn | Thr | Leu | Ser | His | Phe | Pro | Val | Glu | Cys | Pro | Ala | |
| 550 | | | | | 555 | | | | | 560 | | | | | | |
| CCT | CCA | GAA | CCT | GCC | CAG | AGC | TCT | CCA | GGG | GTC | TCT | CAA | AGG | AAA | CTC | 2142 |
| Pro | Pro | Glu | Pro | Ala | Gln | Ser | Ser | Pro | Gly | Val | Ser | Gln | Arg | Lys | Leu | |
| 565 | | | | 570 | | | | | 575 | | | | | | 580 | |
| ATG | CGG | TAC | CAC | TCC | GTG | AGC | ACA | GAG | ACG | CCT | CAT | GAA | CGC | AAG | GAC | 2190 |
| Met | Arg | Tyr | His | Ser | Val | Ser | Thr | Glu | Thr | Pro | His | Glu | Arg | Lys | Asp | |
| | | | | 585 | | | | 590 | | | | | 595 | | | |
| TTT | GAA | TCC | AAA | GCA | AAC | CAC | CTG | GGT | GAC | ACA | GAT | GGG | ACC | CCC | GTG | 2238 |
| Phe | Glu | Ser | Lys | Ala | Asn | His | Leu | Gly | Asp | Thr | Asp | Gly | Thr | Pro | Val | |
| | | | 600 | | | | 605 | | | | 610 | | | | | |
| AAG | ACC | CGG | CGG | CAC | TCG | TGG | AGA | CAG | CAG | ATA | TTC | CTT | CGA | GTG | GCC | 2286 |
| Lys | Thr | Arg | Arg | His | Ser | Trp | Arg | Gln | Gln | Ile | Phe | Leu | Arg | Val | Ala | |
| | | 615 | | | | 620 | | | | 625 | | | | | | |
| ACT | CCA | CAG | AAG | GCT | TGT | GAC | TCC | CCG | AGC | AGA | TAT | GAA | GAT | TAT | TCC | 2334 |
| Thr | Pro | Gln | Lys | Ala | Cys | Asp | Ser | Pro | Ser | Arg | Tyr | Glu | Asp | Tyr | Ser | |
| 630 | | | | | 635 | | | | | 640 | | | | | | |
| GAG | CTG | GGA | GAG | CTC | CCT | CCA | CGC | TCC | CCT | TTA | GAA | CCG | GTG | TGT | GAG | 2382 |
| Glu | Leu | Gly | Glu | Leu | Pro | Pro | Arg | Ser | Pro | Leu | Glu | Pro | Val | Cys | Glu | |
| 645 | | | | 650 | | | | | 655 | | | | | | 660 | |
| GAC | GGC | CCA | TTT | GGC | CAG | TAC | AGG | AAG | AAA | AGA | GGA | AGA | CGT | CAC | GCG | 2430 |
| Asp | Gly | Pro | Phe | Gly | Gln | Tyr | Arg | Lys | Lys | Arg | Gly | Arg | Arg | His | Ala | |
| | | | | 665 | | | | | 670 | | | | | | 675 | |
| AGC | TTC | GAG | AGC | TGT | GGA | AAA | AGG | CCA | TCT | TGC | AGC | AGA | TCC | TGC | CTC | 2478 |
| Ser | Phe | Glu | Ser | Cys | Gly | Lys | Arg | Pro | Ser | Cys | Ser | Arg | Ser | Cys | Leu | |
| | | | 680 | | | | 685 | | | | 690 | | | | | |
| GTC | AGG | ATG | GAG | AAG | GAG | AAT | CAG | AAG | CTA | CAA | GCC | TCT | GAA | AAC | GAT | 2526 |
| Val | Arg | Met | Glu | Lys | Glu | Asn | Gln | Lys | Leu | Gln | Ala | Ser | Glu | Asn | Asp | |
| | | 695 | | | | 700 | | | | 705 | | | | | | |
| TTG | CTG | AAC | AAA | CGC | CTC | AAG | CTT | GAC | TAT | GAA | GAA | ATC | ACT | CCG | TGT | 2574 |
| Leu | Leu | Asn | Lys | Arg | Leu | Lys | Leu | Asp | Tyr | Glu | Glu | Ile | Thr | Pro | Cys | |
| 710 | | | | | 715 | | | | | 720 | | | | | | |
| CTT | AAA | GAA | GTC | ACT | ACA | GTG | TGG | GAA | AAG | ATG | CTT | AGC | ACT | CCA | GGA | 2622 |
| Leu | Lys | Glu | Val | Thr | Thr | Val | Trp | Glu | Lys | Met | Leu | Ser | Thr | Pro | Gly | |
| 725 | | | | | 730 | | | | | 735 | | | | | 740 | |
| AGA | TCC | AAA | ATT | AAG | TTT | GAC | ATG | GAA | AAA | GTG | CAC | TCA | GCT | GTT | GGG | 2670 |
| Arg | Ser | Lys | Ile | Lys | Phe | Asp | Met | Glu | Lys | Val | His | Ser | Ala | Val | Gly | |
| | | | | 745 | | | | 750 | | | | | 755 | | | |
| CAA | GGT | GTG | CCA | CGT | CAT | CAC | CGA | GGT | GAG | ATC | TGG | AAA | TTT | CTA | GCT | 2718 |
| Gln | Gly | Val | Pro | Arg | His | His | Arg | Gly | Glu | Ile | Trp | Lys | Phe | Leu | Ala | |
| | | | 760 | | | | 765 | | | | 770 | | | | | |
| GAG | CAG | TTC | CAC | CTT | AAA | CAC | CCA | TTT | CCT | AGT | AAA | CAG | CAG | CCA | AAG | 2766 |
| Glu | Gln | Phe | His | Leu | Lys | His | Pro | Phe | Pro | Ser | Lys | Gln | Gln | Pro | Lys | |
| | | 775 | | | | 780 | | | | 785 | | | | | | |
| GAC | GTG | CCC | TAC | AAA | GAG | CTC | CTG | AAG | AAG | CTG | ACC | TCG | CAG | CAG | CAC | 2814 |
| Asp | Val | Pro | Tyr | Lys | Glu | Leu | Leu | Lys | Lys | Leu | Thr | Ser | Gln | Gln | His | |
| 790 | | | | | 795 | | | | | 800 | | | | | | |

| | | | | | | | | | | | | | | | | |
|---|---|---|---|---|---|---|---|---|---|---|---|---|---|---|---|---|
| GCC | ATT | CTC | ATC | GAC | CTC | GGG | CGA | ACC | TTT | CCA | ACA | CAT | CCA | TAC | TTC | 2862 |
| Ala | Ile | Leu | Ile | Asp | Leu | Gly | Arg | Thr | Phe | Pro | Thr | His | Pro | Tyr | Phe | |
| 805 | | | | 810 | | | | | 815 | | | | | | 820 | |
| TCT | GCC | CAG | CTT | GGA | GCA | GGT | CAG | CTG | TCA | CTT | TAC | AAC | ATT | CTG | AAG | 2910 |
| Ser | Ala | Gln | Leu | Gly | Ala | Gly | Gln | Leu | Ser | Leu | Tyr | Asn | Ile | Leu | Lys | |
| | | | | 825 | | | | | 830 | | | | | 835 | | |
| GCC | TAC | TCG | CTT | CTG | GAC | CAG | GAG | GTT | GGA | TAC | TGC | CAA | GGT | CTC | AGC | 2958 |
| Ala | Tyr | Ser | Leu | Leu | Asp | Gln | Glu | Val | Gly | Tyr | Cys | Gln | Gly | Leu | Ser | |
| | | | 840 | | | | | 845 | | | | | 850 | | | |
| TTT | GTG | GCA | GGC | ATT | TTG | CTT | CTT | CAC | ATG | AGT | GAG | GAA | GAG | GCG | TTC | 3006 |
| Phe | Val | Ala | Gly | Ile | Leu | Leu | Leu | His | Met | Ser | Glu | Glu | Glu | Ala | Phe | |
| | | 855 | | | | | 860 | | | | | 865 | | | | |
| AAG | ATG | CTC | AAG | TTC | CTG | ATG | TTT | GAC | ATG | GGG | CTG | CGG | AAA | CAG | TAT | 3054 |
| Lys | Met | Leu | Lys | Phe | Leu | Met | Phe | Asp | Met | Gly | Leu | Arg | Lys | Gln | Tyr | |
| | 870 | | | | | 875 | | | | | 880 | | | | | |
| CGG | CCA | GAC | ATG | ATT | ATT | TTG | CAG | ATC | CAG | ATG | TAC | CAG | CTG | TCA | CGG | 3102 |
| Arg | Pro | Asp | Met | Ile | Ile | Leu | Gln | Ile | Gln | Met | Tyr | Gln | Leu | Ser | Arg | |
| 885 | | | | | 890 | | | | | 895 | | | | | 900 | |
| CTC | CTC | CAC | GAT | TAC | CAC | CGA | GAC | CTC | TAC | AAC | CAC | CTG | GAA | GAG | CAC | 3150 |
| Leu | Leu | His | Asp | Tyr | His | Arg | Asp | Leu | Tyr | Asn | His | Leu | Glu | Glu | His | |
| | | | | 905 | | | | | 910 | | | | | 915 | | |
| GAG | ACT | GGC | CCC | CCT | ACG | TAC | GCG | GCT | CCC | TGG | TTT | CTC | ACC | GTG | TTC | 3198 |
| Glu | Thr | Gly | Pro | Pro | Thr | Tyr | Ala | Ala | Pro | Trp | Phe | Leu | Thr | Val | Phe | |
| | | | 920 | | | | | 925 | | | | | 930 | | | |
| GCC | TCA | CAG | TTC | CCA | CTC | GGC | TTT | GTA | GCC | AGA | GTC | TTT | GAT | ATG | ATC | 3246 |
| Ala | Ser | Gln | Phe | Pro | Leu | Gly | Phe | Val | Ala | Arg | Val | Phe | Asp | Met | Ile | |
| | | 935 | | | | | 940 | | | | | 945 | | | | |
| TTC | CTT | CAG | GGA | TCA | GAG | GTC | ATA | TTT | AAA | GTA | GCT | TTA | AGT | CTT | TTG | 3294 |
| Phe | Leu | Gln | Gly | Ser | Glu | Val | Ile | Phe | Lys | Val | Ala | Leu | Ser | Leu | Leu | |
| | 950 | | | | | 955 | | | | | 960 | | | | | |
| GGG | AGC | CAT | AAG | CCC | TTG | ATT | CTA | CAG | CAT | GAG | AAC | CTG | GAA | ACC | ATC | 3342 |
| Gly | Ser | His | Lys | Pro | Leu | Ile | Leu | Gln | His | Glu | Asn | Leu | Glu | Thr | Ile | |
| 965 | | | | | 970 | | | | | 975 | | | | | 980 | |
| GTG | GAC | TTC | ATA | AAG | AAC | ACA | CTC | CCC | AAC | CTG | GGC | CTG | GTG | CAG | ATG | 3390 |
| Val | Asp | Phe | Ile | Lys | Asn | Thr | Leu | Pro | Asn | Leu | Gly | Leu | Val | Gln | Met | |
| | | | | 985 | | | | | 990 | | | | | 995 | | |
| GAG | AAG | ACC | ATC | AGT | CAG | GTG | TTT | GAG | ATG | GAC | ATC | GCC | AAG | CAG | CTC | 3438 |
| Glu | Lys | Thr | Ile | Ser | Gln | Val | Phe | Glu | Met | Asp | Ile | Ala | Lys | Gln | Leu | |
| | | | 1000 | | | | | 1005 | | | | | 1010 | | | |
| CAG | GCC | TAT | GAG | GTC | GAG | TAC | CAC | GTC | GTC | CAG | GAG | GAG | CTT | ATT | GAG | 3486 |
| Gln | Ala | Tyr | Glu | Val | Glu | Tyr | His | Val | Val | Gln | Glu | Glu | Leu | Ile | Glu | |
| | | 1015 | | | | | 1020 | | | | | 1025 | | | | |
| TCC | TCG | CCT | CTC | AGT | GAC | AAC | CAA | AGA | ATG | GAG | AAA | TTG | GAG | AAA | ACC | 3534 |
| Ser | Ser | Pro | Leu | Ser | Asp | Asn | Gln | Arg | Met | Glu | Lys | Leu | Glu | Lys | Thr | |
| | 1030 | | | | | 1035 | | | | | 1040 | | | | | |
| AAC | AGC | ACG | TTG | CGC | AAA | CAG | AAC | CTT | GAC | CTC | CTG | GAG | CAG | TTG | CAG | 3582 |
| Asn | Ser | Thr | Leu | Arg | Lys | Gln | Asn | Leu | Asp | Leu | Leu | Glu | Gln | Leu | Gln | |
| 1045 | | | | | 1050 | | | | | 1055 | | | | | 1060 | |
| GTG | GCA | AAT | GCT | AGG | ATC | CAA | AGC | CTT | GAA | GCC | ACG | GTA | GAG | AAA | CTT | 3630 |
| Val | Ala | Asn | Ala | Arg | Ile | Gln | Ser | Leu | Glu | Ala | Thr | Val | Glu | Lys | Leu | |
| | | | | 1065 | | | | | 1070 | | | | | 1075 | | |
| CTT | ACC | AGC | GAG | AGT | AAG | CTG | AAG | CAG | CGT | GCG | CTG | ACC | CTG | GAG | GTG | 3678 |
| Leu | Thr | Ser | Glu | Ser | Lys | Leu | Lys | Gln | Arg | Ala | Leu | Thr | Leu | Glu | Val | |
| | | | | 1080 | | | | | 1085 | | | | | 1090 | | |
| GAG | CGT | CGC | CCT | GCT | GCA | GAT | GGT | GGA | GGA | GCT | GCG | GAG | GCA | AAG | CGC | 3726 |
| Glu | Arg | Arg | Pro | Ala | Ala | Asp | Gly | Gly | Gly | Ala | Ala | Glu | Ala | Lys | Arg | |
| | | | 1095 | | | | | 1100 | | | | | 1105 | | | |
| CCG | GCC | CAG | CAC | TCC | AGA | GCC | AGA | CTG | CAC | CCA | GCT | GGA | GCC | CAC | AGG | 3774 |
| Pro | Ala | Gln | His | Ser | Arg | Ala | Arg | Leu | His | Pro | Ala | Gly | Ala | His | Arg | |
| | | 1110 | | | | | 1115 | | | | | 1120 | | | | |

-continued

```
CGA TTG ACC GCT GCC AGA AGA GAC TGT GCA CCA TTA ACA CTG TCC AAG      3822
Arg Leu Thr Ala Ala Arg Arg Asp Cys Ala Pro Leu Thr Leu Ser Lys
1125                1130                1135                1140

CCT TAA TCAAGAGAGA TGGAAGTCAG AGGCAGAGAA GAGAGAACTT CTCAGGGAGG       3878
Pro *

AAACTGGCTG ACCAGCCTGC AGATCCTTTT GAGCTCAGAA CTTGGGATTG GAGGACAAAA    3938

GTCTCAGAGT TATTGTTGTT TTTGGTTCTA ATCCGTCCCC TTTCCAGTCC TGGTTGTTGT    3998

AGCTTTAGAT GGCATGGACA TGAATAAATT ACATTTATGG C                       4039
```

( 2 ) INFORMATION FOR SEQ ID NO:2:

( i ) SEQUENCE CHARACTERISTICS:
        ( A ) LENGTH: 1141 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Pro Met Leu Pro Trp Val Val Ala Glu Val Arg Arg Leu Ser Gly
  1               5                  10                  15

Gln Cys Ser Lys Lys Glu Pro Arg Thr Lys Gln Val Arg Leu Trp Val
             20                  25                  30

Ser Pro Ser Gly Leu Arg Cys Glu Pro Asp Leu Glu Lys Ser Gln Pro
         35                  40                  45

Trp Asp Pro Leu Ile Cys Ser Ser Ile Phe Glu Cys Lys Pro Gln Arg
     50                  55                  60

Val His Lys Leu Ile His Asn Ser His Asp Pro Ser Tyr Phe Ala Cys
 65                  70                  75                  80

Leu Ile Lys Glu Asp Ala Ala His Arg Gln Ser Leu Cys Tyr Val Phe
                 85                  90                  95

Lys Ala Asp Asp Gln Thr Lys Val Pro Glu Ile Ile Ser Ser Ile Arg
                100                 105                 110

Gln Ala Gly Lys Ile Ala Arg Gln Glu Glu Leu Arg Cys Pro Ser Glu
            115                 120                 125

Phe Asp Asp Thr Phe Ala Lys Lys Phe Glu Val Leu Phe Cys Gly Arg
        130                 135                 140

Val Thr Val Ala His Lys Lys Ala Pro Pro Ala Leu Ile Asp Glu Cys
145                 150                 155                 160

Ile Glu Lys Phe Asn His Val Ser Cys Gly Arg Arg Thr Asp Trp Glu
                165                 170                 175

Ala Pro Thr Gly Gln Pro Ser Ala Pro Gly Pro Arg Pro Met Arg Lys
            180                 185                 190

Ser Phe Ser Gln Pro Gly Leu Arg Ser Leu Ala Phe Arg Lys Glu Phe
        195                 200                 205

Gln Asp Ala Ser Leu Arg Ser Ser Thr Phe Ser Ser Phe Asp Asn Asp
    210                 215                 220

Ile Glu Asn His Leu Ile Gly Gly His Asn Val Gln Pro Thr Asp
225                 230                 235                 240

Met Glu Glu Asn Arg Thr Met Leu Phe Thr Ile Gly Pro Ser Glu Val
                245                 250                 255

Tyr Leu Ile Ser Pro Asp Thr Lys Lys Ile Ala Leu Glu Lys Asn Phe
            260                 265                 270

Lys Glu Ile Ser Phe Cys Ser Gln Gly Ile Arg His Val Asp His Phe
        275                 280                 285

Gly Phe Ile Cys Arg Glu Cys Ser Gly Gly Gly Ser Gly Gly Phe His
```

-continued

|     | 290 |     |     |     | 295 |     |     |     | 300 |     |     |     |     |
| --- | --- | --- | --- | --- | --- | --- | --- | --- | --- | --- | --- | --- | --- |
| Phe 305 | Val | Cys | Tyr | Val | Phe 310 | Gln | Cys | Thr | Asn 315 | Glu | Ala | Leu | Val | Asp | Glu 320 |
| Ile | Met | Met | Thr | Leu 325 | Lys | Gln | Ala | Phe | Thr 330 | Val | Ala | Ala | Val | Gln 335 | Gln |
| Thr | Ala | Lys | Ala 340 | Pro | Ala | Gln | Leu | Cys 345 | Glu | Gly | Cys | Pro | Leu 350 | Gln | Gly |
| Leu | His | Lys 355 | Leu | Cys | Glu | Arg | Ile 360 | Glu | Gly | Met | Asn | Ser 365 | Ser | Lys | Thr |
| Lys | Leu 370 | Glu | Leu | Gln | Lys | His 375 | Leu | Thr | Thr | Leu | Thr 380 | Asn | Gln | Glu | Gln |
| Ala 385 | Thr | Ile | Phe | Glu | Glu 390 | Val | Gln | Lys | Leu | Arg 395 | Pro | Arg | Asn | Glu | Gln 400 |
| Arg | Glu | Asn | Glu | Leu 405 | Ile | Ile | Ser | Phe | Leu 410 | Arg | Cys | Leu | Tyr | Glu 415 | Glu |
| Lys | Gln | Lys | Glu 420 | His | Ser | His | Thr | Gly 425 | Ala | Pro | Lys | Gln | Thr 430 | Leu | Gln |
| Val | Ala | Ala 435 | Glu | Asn | Ile | Gly | Ser 440 | Asp | Leu | Pro | Pro | Ser 445 | Ala | Ser | Arg |
| Phe | Arg 450 | Leu | Asp | Ser | Leu | Lys 455 | Asn | Arg | Ala | Lys | Arg 460 | Ser | Leu | Thr | Glu |
| Ser 465 | Leu | Glu | Ser | Ile | Leu 470 | Ser | Arg | Gly | Asn | Lys 475 | Ala | Arg | Gly | Leu | Gln 480 |
| Asp | His | Ser | Ala | Ser 485 | Val | Asp | Leu | Asp | Ser 490 | Ser | Thr | Ser | Ser | Thr 495 | Leu |
| Ser | Asn | Thr | Ser 500 | Lys | Glu | Leu | Ser | Met 505 | Gly | Asp | Lys | Glu | Ala 510 | Phe | Pro |
| Val | Ser | Glu 515 | Thr | Ser | Phe | Lys | Leu 520 | Leu | Gly | Ser | Ser | Asp 525 | Asp | Leu | Ser |
| Ser | Asp 530 | Ser | Glu | Gly | His | Ile 535 | Ala | Glu | Glu | Ser | Ala 540 | Leu | Leu | Ser | Pro |
| Gln 545 | Gln | Ala | Phe | Arg | Arg 550 | Arg | Ala | Asn | Thr | Leu 555 | Ser | His | Phe | Pro | Val 560 |
| Glu | Cys | Pro | Ala | Pro 565 | Pro | Glu | Pro | Ala | Gln 570 | Ser | Ser | Pro | Gly | Val 575 | Ser |
| Gln | Arg | Lys | Leu 580 | Met | Arg | Tyr | His | Ser 585 | Val | Ser | Thr | Glu | Thr 590 | Pro | His |
| Glu | Arg | Lys 595 | Asp | Phe | Glu | Ser | Lys 600 | Ala | Asn | His | Leu | Gly 605 | Asp | Thr | Asp |
| Gly | Thr 610 | Pro | Val | Lys | Thr | Arg 615 | Arg | His | Ser | Trp | Arg 620 | Gln | Gln | Ile | Phe |
| Leu 625 | Arg | Val | Ala | Thr | Pro 630 | Gln | Lys | Ala | Cys | Asp 635 | Ser | Pro | Ser | Arg | Tyr 640 |
| Glu | Asp | Tyr | Ser | Glu 645 | Leu | Gly | Glu | Leu | Pro 650 | Pro | Arg | Ser | Pro | Leu 655 | Glu |
| Pro | Val | Cys | Glu 660 | Asp | Gly | Pro | Phe | Gly 665 | Gln | Tyr | Arg | Lys | Lys 670 | Arg | Gly |
| Arg | Arg | His 675 | Ala | Ser | Phe | Glu | Ser 680 | Cys | Gly | Lys | Arg | Pro 685 | Ser | Cys | Ser |
| Arg | Ser 690 | Cys | Leu | Val | Arg | Met 695 | Glu | Lys | Glu | Asn | Gln 700 | Lys | Leu | Gln | Ala |
| Ser 705 | Glu | Asn | Asp | Leu | Leu 710 | Asn | Lys | Arg | Leu | Lys 715 | Leu | Asp | Tyr | Glu | Glu 720 |

```
Ile  Thr  Pro  Cys  Leu  Lys  Glu  Val  Thr  Thr  Val  Trp  Glu  Lys  Met  Leu
               725                      730                      735

Ser  Thr  Pro  Gly  Arg  Ser  Lys  Ile  Lys  Phe  Asp  Met  Glu  Lys  Val  His
               740                      745                      750

Ser  Ala  Val  Gly  Gln  Gly  Val  Pro  Arg  His  His  Arg  Gly  Glu  Ile  Trp
               755                      760                      765

Lys  Phe  Leu  Ala  Glu  Gln  Phe  His  Leu  Lys  His  Pro  Phe  Pro  Ser  Lys
               770                      775                      780

Gln  Gln  Pro  Lys  Asp  Val  Pro  Tyr  Lys  Glu  Leu  Leu  Lys  Lys  Leu  Thr
785                      790                      795                      800

Ser  Gln  Gln  His  Ala  Ile  Leu  Ile  Asp  Leu  Gly  Arg  Thr  Phe  Pro  Thr
               805                      810                      815

His  Pro  Tyr  Phe  Ser  Ala  Gln  Leu  Gly  Ala  Gly  Gln  Leu  Ser  Leu  Tyr
               820                      825                      830

Asn  Ile  Leu  Lys  Ala  Tyr  Ser  Leu  Leu  Asp  Gln  Glu  Val  Gly  Tyr  Cys
               835                      840                      845

Gln  Gly  Leu  Ser  Phe  Val  Ala  Gly  Ile  Leu  Leu  Leu  His  Met  Ser  Glu
     850                      855                      860

Glu  Glu  Ala  Phe  Lys  Met  Leu  Lys  Phe  Leu  Met  Phe  Asp  Met  Gly  Leu
865                      870                      875                      880

Arg  Lys  Gln  Tyr  Arg  Pro  Asp  Met  Ile  Ile  Leu  Gln  Ile  Gln  Met  Tyr
               885                      890                      895

Gln  Leu  Ser  Arg  Leu  Leu  His  Asp  Tyr  His  Arg  Asp  Leu  Tyr  Asn  His
               900                      905                      910

Leu  Glu  Glu  His  Glu  Thr  Gly  Pro  Pro  Thr  Tyr  Ala  Ala  Pro  Trp  Phe
               915                      920                      925

Leu  Thr  Val  Phe  Ala  Ser  Gln  Phe  Pro  Leu  Gly  Phe  Val  Ala  Arg  Val
               930                      935                      940

Phe  Asp  Met  Ile  Phe  Leu  Gln  Gly  Ser  Glu  Val  Ile  Phe  Lys  Val  Ala
945                      950                      955                      960

Leu  Ser  Leu  Leu  Gly  Ser  His  Lys  Pro  Leu  Ile  Leu  Gln  His  Glu  Asn
               965                      970                      975

Leu  Glu  Thr  Ile  Val  Asp  Phe  Ile  Lys  Asn  Thr  Leu  Pro  Asn  Leu  Gly
               980                      985                      990

Leu  Val  Gln  Met  Glu  Lys  Thr  Ile  Ser  Gln  Val  Phe  Glu  Met  Asp  Ile
               995                     1000                     1005

Ala  Lys  Gln  Leu  Gln  Ala  Tyr  Glu  Val  Glu  Tyr  His  Val  Val  Gln  Glu
     1010                     1015                     1020

Glu  Leu  Ile  Glu  Ser  Ser  Pro  Leu  Ser  Asp  Asn  Gln  Arg  Met  Glu  Lys
1025                     1030                     1035                     1040

Leu  Glu  Lys  Thr  Asn  Ser  Thr  Leu  Arg  Lys  Gln  Asn  Leu  Asp  Leu  Leu
               1045                     1050                     1055

Glu  Gln  Leu  Gln  Val  Ala  Asn  Ala  Arg  Ile  Gln  Ser  Leu  Glu  Ala  Thr
               1060                     1065                     1070

Val  Glu  Lys  Leu  Leu  Thr  Ser  Glu  Ser  Lys  Leu  Lys  Gln  Arg  Ala  Leu
               1075                     1080                     1085

Thr  Leu  Glu  Val  Glu  Arg  Arg  Pro  Ala  Ala  Asp  Gly  Gly  Gly  Ala  Ala
               1090                     1095                     1100

Glu  Ala  Lys  Arg  Pro  Ala  Gln  His  Ser  Arg  Ala  Arg  Leu  His  Pro  Ala
1105                     1110                     1115                     1120
```

```
Gly Ala His Arg Arg Leu Thr Ala Ala Arg Arg Asp Cys Ala Pro Leu
            1125                    1130                1135
Thr Leu Ser Lys Pro
            1140
```

TBC1 GENE AND USES THEREOF

STATEMENT AS TO FEDERALLY SPONSORED RESEARCH

This invention was made at least in part with funds from the Federal government, and the government therefore has certain rights in the invention.

BACKGROUND OF THE INVENTION

This invention relates to recombinant mammalian nucleic acids and polypeptides and uses thereof to diagnose and treat leukemias. The invention also relates to methods for diagnosing spermatogenesis disorders.

Acute myelogenous leukemia (AML) is a clonal hemopathy in which cell proliferation is not coupled to differentiation. Thus, precursor cells fail to mature, resulting in uncontrolled proliferation of one or more clonal populations. Several subtypes of AML exist and are designated $M_1$–$M_7$ (Table 1). Generally, the classification is based upon the type of cell affected. For example, acute erythroleukemia (AEL), also known as DiGuglielmo's syndrome, affects progenitors of erythrocytes and is designated $M_6$. Acute megakaryoblastic leukemia (AMegL), also known as malignant myelosclerosis, affects megakaryocytes and is designated $M_7$.

TABLE 1

| Class | Description |
| --- | --- |
| $M_1$ | Acute myeloblastic leukemia without maturation |
| $M_2$ | Acute myeloblastic leukemia with maturation |
| $M_3$ | Acute hypergranular promyelocytic leukemia |
| $M_4$ | Acute myelomonocytic leukemia (well differentiated) With abnormal marrow eosinophils ($M_4$Eo) |
| $M_5$ | Acute monocytic leukemia (poorly differentiated) More than 80 percent monoblasts ($M_{5a}$) More than 20 percent promonocytes and monocytes ($M_{5b}$) |
| $L_1$ | Acute lymphocytic leukemia (common childhood variant - homogeneous population) |
| $L_2$ | Acute lymphocytic leukemia (common adult variant - heterogeneous population) |
| $L_3$ | Burkitt's cell type |

The assignment of a leukemia to a particular subtype is based on an analysis of bone marrow or blood morphology by Romanovsky staining or other cytochemical assays. For example, a diagnosis of $M_6$ leukemia commonly is made, at least in part, on the basis of the pattern of red staining observed in the periodic acid-Schiff reaction. In addition to classifications based on cell staining, AMLs are classified on the basis of monoclonal antibody reactivity to cell surface markers and differentiation antigens. For example, monoclonal antibodies against glycophorin A and against spectrin are useful for diagnosing $M_6$ leukemia. Similarly, anti-platelet GPIIb/IIIa and anti-platelet GPIb antibodies can be used in a diagnosis of $M_7$ leukemia.

Current methods for treating leukemias include cytotoxic chemotherapy, post-ablation marrow transplant, and combination chemotherapy plus irradiation. Other therapies include those which are designed to inhibit cell proliferation and provoke cells to differentiate. For example, all-trans retinoic acid has been used to effectively treat patients afflicted with acute promyelocytic leukemia ($M_3$); this drug causes the cell to exit the mitotic phase and differentiate (Castaigne et al., 1990, Blood 76: 1704–1709; Meng-er et al., 1988, Blood 72: 567–572). It has also been suggested that the efficacy of the nucleoside analog cytarabine is due to stimulation of differentiation (Wisch et al., N. E. J. Of Med., 1983 26:1599–1062).

Normally, cellular differentiation is tightly coupled to regulation of the cell cycle. Differentiation involves activation of cell-specific genes in proliferating progenitors during distinct phases of the cell cycle. In addition to AML, other diseases are characterized by the inability of a progenitor cell to complete the mitotic phase and properly differentiate. For example, testicular maturation arrest (TMA) is a spermatogenesis disorder in which immature and infertile sperm cells are produced.

In the normal development of spermatozoa, a spermatogonium undergoes several mitotic divisions and then differentiates into a diploid primary spermatocyte. The primary spermatocyte then undergoes a first meiotic division to produce two haploid secondary spermatocytes which, upon a second meiotic division, produce four spermatids. In the final stage of spermatogenesis, termed spermiogenesis, the spermatids differentiate and become mature spermatozoa. In patients afflicted with TMA, spermatogenesis is prematurely halted, giving rise to primary and secondary spermatocytes which are infertile. Commonly, a diagnosis of TMA is made on the basis of the absence of mature spermatozoa in seminal fluid and the detection of primary and secondary spermatocytes in testicular tissue. The detection of primary and secondary spermatocytes serves to distinguish TMA from the spermatogenesis disorder azoospermia which is characterized by the absence of developing sperm cells.

SUMMARY OF THE INVENTION

I have cloned for the first time a gene, the Tbc1 gene (for tre-2, BUB2, and cdc16), which encodes a protein which is involved in coupling cell proliferation to cell differentiation. The Tbc1 protein is differentially expressed during the maturation of erythrocytes, megakaryoblasts, and germ cells. Thus, the Tbc1 level is a useful marker of proper differentiation of those cell types. In addition, I have discovered that Tbc1 is related to BUB2 and cdc16 which are regulators of the cell cycle. The cell cycle-regulating properties of Tbc1 make it useful for modulating the proliferation of certain leukemic cells. By causing cells to differentiate, Tbc1 can be used as a therapeutic for certain leukemias.

Accordingly, in one aspect, the invention features a method of treating leukemias other than the $M_6$ and $M_7$ classes in a patient (e.g., a human), involving administering to the patient a therapeutically effective amount of Tbc1.

In preferred embodiments, Tbc1 is used to treat an acute myelogenous leukemia classified as $M_1$, $M_2$, $M_3$, $M_4$, $M_5$, $L_1$, $L_2$, or $L_3$. In other preferred embodiments, Tbc1 is expressed from a retroviral or adenoviral vector engineered for expression of Tbc1. For example, the Tbc1 gene can be located on a viral vector (e.g., and adeno-associated virus) such that it is operably linked to a promoter capable of inducing Tbc1 expression in hematopoietic stem cells. Standard techniques of transducing hematopoietic stem cells can be used for expression of Tbc1 (e.g., electroporation).

The invention also features a method of diagnosing leukemias of erythrocytic or megakaryocytic lineages in a patient (e.g., a human); the method involves assaying for expression of Tbc1 in a leukemic cell; expression of Tbc1 in the leukemic cell indicates that the leukemia is of erythrocytic or megakaryocytic origin. Assays for Tbc1 expression can be used in conjunction with other methods of determining cell lineage and diagnosing leukemia. For example, a diagnosis of erythrocytic leukemia can be made by assaying for Tbc1 expression in bone marrow or blood samples in addition to assaying for reactivity with erythrocyte-specific antibodies (e.g., anti-glycophorin A or anti-spectrin antibodies). Other standard indicators of leukemia, such as cell morphology, can also be used in the diagnosis. Tbc1 expression can be measured by assaying for Tbc1 RNA; the presence of Tbc1 RNA indicates that the cell is of an erythrocytic or megakaryocytic lineage. Suitable assays for measuring RNA include Northern blot analysis, slot and dot blot analysis, RT-PCR, and in situ hybridizations. Appropriate probes, and methods for preparing them, will be apparent from the description of the Tbc1 gene below. The Tbc1 protein can also be detected in an immunoassay of bone marrow or blood samples; appropriate immunoassays include immunoperoxidase staining, immunofluorescence, western blot analysis, ELISA.

The invention further features a method of diagnosing a spermatogenesis disorder in a patient (e.g., a human); the method involves detecting primary and secondary spermatocytes in testicular tissue of the patient by assaying for Tbc1 expression. A decreased level of Tbc1 relative to normal levels is indicative of the absence or abnormality of primary and/or secondary spermatocytes. A normal level of Tbc1 in testicular tissue and the absence of spermatozoa in seminal fluid is indicative of a spermatogenesis disorder in which maturation of primary and secondary spermatocytes into spermatozoa is halted.

The level of Tbc1 expression can be determined by measuring Tbc1 RNA or protein levels. Suitable assays for measuring RNA levels include Northern blot analysis, slot and dot blot analysis, and in situ hybridization. Appropriate probes, and methods for preparing them, will be apparent from the description of the Tbc1 gene below. The level of Tbc1 can also be measured in an immunoassay of testicular tissue; appropriate immunoassays include immunoperoxidase staining, immunofluorescence assays, western blot analysis, RIA, and ELISA.

The invention further features substantially pure DNA (e.g., genomic DNA, cDNA, or synthetic DNA) encoding a Tbc1 polypeptide. The DNA of the invention has a sequence having about 80% or greater sequence identity to the DNA sequence of FIG. 1 (SEQ ID NO: 1) and encoding a polypeptide substantially identical to Tbc1 polypeptide of FIG. 1 (SEQ ID NO: 2).

In another aspect, the invention features a substantially pure Tbc1 polypeptide. Preferably, the polypeptide includes a greater than 50 amino acid sequence substantially identical to a greater than 50 amino acid sequence shown in FIG. 1.

The invention also features antibodies, including monoclonal antibodies, which bind specifically to a Tbc1 polypeptide. Such antibodies can be generated by standard techniques employing the substantially purified Tbc1 protein, or fragments thereof, described herein. For example, antibodies directed against Tbc1 can be produced by inoculating the mammal (e.g., a rabbit or a mouse) with substantially purified Tbc1. Anti-Tbc1 antibodies can be detected by any of several methods known to those skilled in the art (e.g., by ELISA, RIA, immunoprecipitation, immunostaining, fluorescent immunoassays, Western blot immunoassay, slot or dot blot assays, or Ouchterlony assays).

By "polypeptide" is meant any chain of amino acids, regardless of length or post-translational modification (e.g., glycosylation or phosphorylation).

By "substantially identical" is meant a polypeptide or nucleic acid exhibiting at least 50%, preferably 80%, more preferably 90%, and most preferably 95% sequence identity to a reference amino acid or nucleic acid sequence. For polypeptides, the length of comparison sequences will generally be at least 16 amino acids, preferably at least 20 amino acids, more preferably at least 25 amino acids, and most preferably at least 35 amino acids. For nucleic acids, the length of comparison sequences will generally be at least 50 nucleotides, preferably at least 60 nucleotides, more preferably at least 75 nucleotides, and most preferably at least 100 nucleotides.

Sequence identity is typically measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various substitutions, deletions, substitutions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

By "substantially pure polypeptide" is meant a Tbc1 polypeptide which has been separated from components which naturally accompany it. Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, Tbc1 polypeptide. A substantially pure Tbc1 polypeptide may be obtained, for example, by extraction from a natural source (e.g., a hematopoietic cell, a spermatocyte, or a kidney cell); by expression of a recombinant nucleic acid encoding a Tbc1 polypeptide; or by chemically synthesizing the protein. Purity can be measured by any appropriate method, (e.g., column chromatography, polyacrylamide gel electrophoresis, or HPLC analysis).

A protein is substantially free of naturally associated components when it is separated from those contaminants which accompany it in its natural state. Thus, a protein which is chemically synthesized or produced in a cellular system different from the cell from which it naturally originates will be substantially free from its naturally associated components. Accordingly, substantially pure polypeptides include those derived from eukaryotic organisms but synthesized in E. coli or other prokaryotes.

By "substantially pure DNA" is meant DNA that is free of the genes which, in the naturally-occurring genome of the organism from which the DNA of the invention is derived, flank the gene. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence.

By "spermatogenesis disorder" is meant a condition which is characterized by the inability of a male mammal to complete the normal process of producing spermatozoa. Examples of spermatogenesis disorders are TMA and azoospermia.

By "stem cell" is meant any cell whose daughter cells can differentiate into other cell types. Examples of stem cells are multipotential stem cells, myeloid stem cells, and lymphoid stem cells.

DETAILED DESCRIPTION

The drawings will first be described.

BRIEF DESCRIPTION OF THE DRAWINGS

FIG. 1 is a listing of the nucleotide and predicted amino acid sequences of Tbc1 (SEQ ID NO: 1 and SEQ ID NO: 2, respectively), FIG. 2A–F is a series of micrographs which show the morphology of P815 mastocytoma cells and the GATA-1-expressing P815 subline, PGT6. P815 (panels A, C, and E) and PGT6 cells (panels B, D, and F) were stained with Wright-Geimsa (panels A and B) or toluidine blue (panels C and D). Panels E and F display the increased density of the granules which are characteristic of mast cell differentiation in the PGT6 subline.

The Tbc1 Gene

Figure 3:
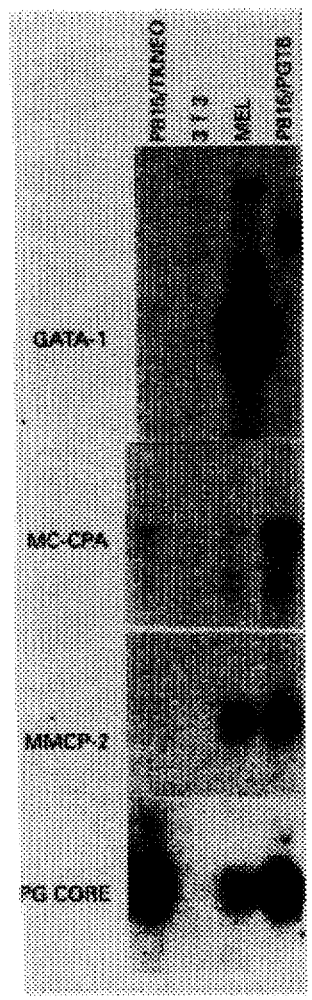
FIG. 3 is a photograph of an autoradiogram obtained from Northern blot analysis of P815 and PGT6 cells. The probes which were used in this analysis are listed to the left of the photograph.

The cloned Tbc1 gene of the invention can be used to inhibit mitosis in a leukemic cell and allow the cell to differentiate. In addition, methods which measure the level of Tbc1 expression are useful for detecting primary and secondary spermatocytes and diagnosing infertility. Such methods also are useful for detecting cells of erythrocytic and megakaryoblastic lineages, and thus the methods are useful in the diagnosis of erythrocytic and megakaryoblastic leukemias (e.g., $M_6$ and $M_7$ leukemias).

There now follows a description of the cloning and characterization of a murine Tbc1 genomic DNA, the Tbc1cDNA, RNA, protein, and pattern of expression. Briefly, a subtractive approach was used to identify a gene which is involved in the differentiation of progenitor cells into mature cells. RNAs of differentially expressed genes were isolated by enforced expression of the transcription factor GATA-1 in undifferentiated P815 mast cells. GATA-1 controls the expression of genes which are involved in mast cell differentiation, and expression of GATA-1 in the P815 cell line caused sublines of P815 cells (e.g., PGT6) to be more differentiated than the P815 cells. Subtracted cDNA prepared from the parental P815 cell line and the PGT6 subline was used to screen mast cell cDNA libraries. This procedure resulted in the identification of the Tbc1 gene. The pattern of Tbc1 expression, subcellular localization, and sequence similarity to regulators of the cell cycle indicate that Tbc1 is a biochemical marker for cellular differentiation, a negative regulator of the cell cycle, and a mediator of cellular differentiation.

Isolation of a Subtracted cDNA Probe

Cells: P815 cells (ATCC deposit # TIB64) and Murine Erythroleukemia (MEL) cells (NIMGS # $GM_{086}$) were cultured in Dulbecco's modified Eagle's medium supplemented with 10% fetal calf serum, 10 mM HEPES, 2 mM glutamine, 50 units/ml penicillin, and 50 mg/ml streptomycin. The PGT6 subline was produced by transfecting P815 cells with an expression plasmid encoding the murine GATA-1 cDNA (Tsai et al., 1989, Nature, 339:446–451), and selecting for neomycin-resistant clones. Primary cultures of murine bone marrow-derived mast cells (BMMC) were grown for 3–4 weeks in 50% WEHI-3 cell-conditioned medium and 50% enriched medium.

Isolation of mast cell cDNAs encoding potential targets of GATA-1: Transfection of P815 cells with a GATA-1 expression vector containing the neomycin resistance gene resulted in G418-resistant stable cell lines that expressed GATA-1 RNA and protein. Several independent lines had an increase in cytoplasmic granules compared with the parent P815 cell line (FIG. 2). Sublines with an increased number of granules also adhered more strongly to the culture dish. One of these sublines, PGT6, is described in detail.

To assay for an increase in cytoplasmic granules, cells were transferred to glass slides by centrifugation in a cytospin (Shandon) at 400 rpm for 5 min. The slides were then air-dried, fixed with methanol, and stained with Wright-Geimsa or toluidine blue by standard techniques. For electron microscopy, cells were pelleted at 500×g, placed into Hirsh fixative, dehydrated through a series of graded alcohols, infiltrated and embedded in Epon-812. Sections were stained with uranyl acetate and lead citrate, and viewed with an electron microscope by standard methods.

Electron microscopic analysis indicated that the parental (P815) and PGT6 cell lines represent two distinct stages of mast cell differentiation. PGT6 cells show an increased number and density of granules compared with P815 cells.

The PGT6 cell line was further characterized by Northern blot analysis. Except as noted, Northern blot analysis was performed using standard methods and 1–2 µg of poly-A+ RNA on a 1% agarose/formaldehyde gel. RNA was transferred to, and immobilized on, a charged nylon membrane. Hybridizations were performed overnight at 42° C. in 50% formaldehyde, 6× SSC, 2× Denhardt's buffer, and 100–200 µg/ml of denatured salmon sperm DNA.

Northern blot analysis (FIG. 3) demonstrated that GATA-1 RNA was expressed in PGT6 cells, while no GATA-1 RNA was detected in the control cells (transfected P815 cells and NIH 3T3 cells). Murine erythroleukemia (MEL) cells expressed endogenous GATA-1. In addition, two mast cell-specific proteases, mast cell carboxypeptidase A (MC-CPA) and mouse mast cell protease 2 (MMCP-2), were expressed at a higher level in the GATA-1 expressing PGT6 cells than in the parent cell line. The level of expression of the proteoglycan core peptide gene was not affected in the GATA-1 expressing cells (FIG. 3), and thus these data indicate that activation of the mast cell program in the PGT6 cell line affected a specific subset of genes. Because the P815 and PGT6 cell lines are genetically identical except for the enforced expression of GATA-1 in PGT6 cells, a subtractive approach was used to identify target genes of the GATA-binding proteins.

Probe preparation by cDNA subtraction: A subtractive probe was produced using The Subtractor Kit™, subtractive RNA purification kit (Invitrogen) and mRNA isolated from P815 and PGT6 cells. First strand cDNA was synthesized from PGT6 mRNA using oligo dT and reverse transcriptase (48° C. for 45 minutes). The subtracted probe was produced by hybridization of the PGT6-derived cDNA to a twentyfold excess of photobiotinylated P815 mRNA at 68° C. for 24–48 hr. Hybridized nucleic acids were bound to streptavidin and extracted with phenol/chloroform; the resulting subtracted pool of cDNA was randomly labeled and used to probe mast cell cDNA libraries.

Construction and screening of mast cell cDNA libraries: The bone marrow-derived mast cell (BMMC) cDNA library employed in these experiments (provided by M. Gurish (Harvard Medical School)) was derived from a Kirsten virus-transformed mast cell line and made from mRNA of day 21 cultures of primary bone-marrow derived mast cells. First and second strand cDNA were synthesized using the Time Saver™ cDNA synthesis kit (Pharmacia). NotI/EcoRI adaptors then were attached to the cDNA, and the cDNA was cloned into the lambda Zap II vector (Stratagene).

Phage containing the mast cell cDNAs were plated at low density (5–10,000 pfu/plate), and filters having the mast cell cDNAs were incubated with the subtracted probe at 68°0 C. overnight in 6× SSC, 2× Denhardt's buffer, and 200 µg/ml denatured salmon sperm DNA. Approximately 50 plaques were positive in this assay. cDNA inserts of these plaques were obtained by PCR using primers derived from the sequence of the phage arms. These inserts were nick-translated and used as probes in Northern blot analysis to confirm that expression of the corresponding DNA was higher in the PGT6 cells than in the P815 cells.

Northern blot analysis demonstrated that expression of each cDNA was increased 2–20 fold in the PGT6 subline relative to the level of expression found in the P815 cell line. cDNAs which showed relatively high expression by Northern blot analysis were subcloned into Bluescript SK- (Stratagene), sequenced by the dideoxy method, and, using the BLAST program, compared with DNAs found in the Genbank and dBest data bases. The nucleotide sequence of several isolated cDNAs were identical to previously-cloned mast cell-specific or hematopoietic-specific cDNAs such as MC-CPA, MMCP-5 and gp49 (Table 2). Most of the isolated cDNAs were novel and had little or no homology to sequences in the databases which were searched.

TABLE 2

Previously isolated genes that were expressed at higher levels in PGT6 compared to P815 cells.

| Gene | Fold induction* | Number of isolates |
|---|---|---|
| MC-CPA | 25 | 8 |
| MMCP-5 | 6.5 | 2 |
| gp49 | 4.2 | 1 |
| 37 | 3.3 | 1 |
| prion | 2.8 | 1 |

*fold induction of PGT6/P815 was determined using phosphorimage analysis (Molecular Dynamics) of Northern blots normalized for loading with actin mRNA levels.

Figure 4A:
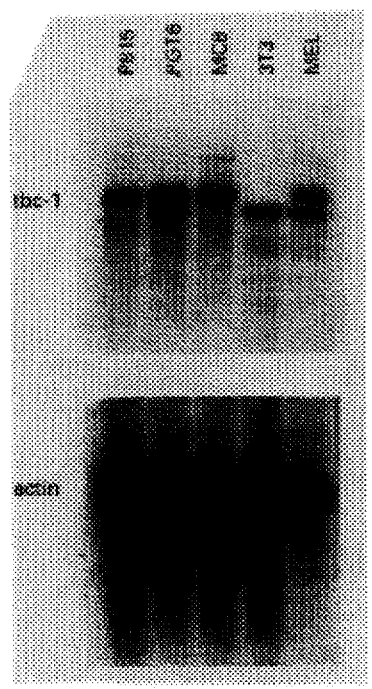
FIG. 4A–D is a series of photographs of autoradiograms obtained from Northern blot analysis of Tbc1 mRNA in several cell lines and tissues.
Figure 4B:

Northern blot analysis of one cDNA clone, designated Tbc1, demonstrated two distinct RNA transcripts (upper and lower). One lower transcript was expressed more highly in PGT6 cells compared with the level found in P815 cells (FIG. 4A). A single lower RNA transcript was detected in NIH 3T3 cells, while the erythroid cell line (MEL) expressed both transcripts. The mast cell line MC8 and bone marrow-derived mast cells predominantly expressed the upper transcript (FIGS. 4A and 4B).

Figure 4C:
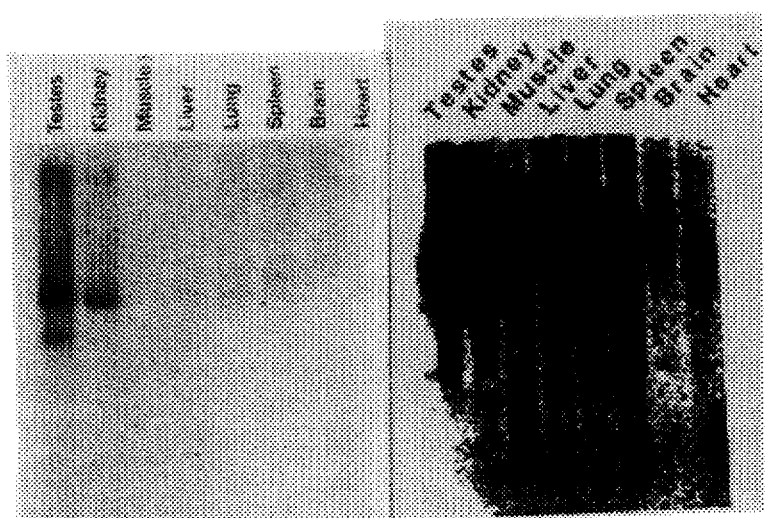
Figure 4D:
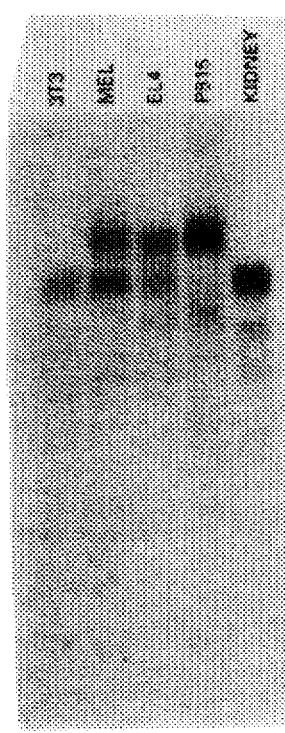

Northern blot analysis of several mouse tissues revealed a diverse pattern of Tbc1 expression with different sized transcripts expressed in specific tissues. Tbc1 was highly expressed in testis and kidney, and related transcripts were expressed at lower levels in lung, spleen, brain, and heart (FIG. 4C). A hematopoietic-specific transcript (FIG. 4D, the upper band) is present in many blood cell lines, distinguishing Tbc1 transcripts of hematopoietic cells from Tbc1 transcripts of kidney cells.

The original isolate of Tbc1 was a partial cDNA of 3.4 kb which contained an internal EcoRI site (at nucleotide 1490). An 850 bp EcoRI cDNA fragment corresponding to the 5' end was used to screen additional libraries to obtain overlapping clones for the construction of a full-length cDNA. The most 5' sequence obtained was derived from a murine kidney library and included a 1.4 kb clone. The sequence of Tbc1 is shown in FIG. 1. Two methionines (at nucleotides 403 and 409) are in frame and have reasonable Kozak consensus sequences, indicating potential translation initiation sites. A stop codon is present at nucleotide 3826. The protein product of the open reading frame is predicted to be 1141 amino acids in length with a molecular weight of 129 kD. The cDNA did not contain a polyadenylation sequence.

Tbc1 is a novel protein that defines a new family of polypeptides: I have found that Tbc1 is a member of a family of related proteins which share a domain of 180–200 amino acids. Comparative searches (BLAST) of conventional databases demonstrated that Tbc1 shows sequence identity to a open reading frame 1 of the tre-2 oncogene. Regions of Tbc1 outside of this domain demonstrate no significant identity to the tre-2 oncogene. Both the Tbc1 and tre-2 polypeptide sequences were used as queries of the dBest database to obtain tagged sequences that showed sequence identity. Several tagged sequences demonstrated sequence identity, and these were then used to search for related sequences in the protein databases. This search demonstrated sequence identity to two yeast genes that are involved in the regulation of mitosis during the cell cycle, BUB2 and cdc16. Each member of the family has the 180–200 amino acid domain, which I refer to as the TBC domain (for tre-2, BUB2 and cdc16) The TBC1 domain is encoded by nucleotide 2692–3258 of Tbc1.

BUB2 and cdc16 are phosphoproteins, and several tyrosine residues are conserved in the TBC domain. The N-terminus of Tbc1 contains stretches of cysteines and histidines which are characteristic of zinc finger structures. In addition, there are short stretches of basic amino acids in the N-terminus which are characteristic of nuclear localization signals (amino acids 61–66 and 264–273). The C-terminus of the Tbc1 protein contains a long stretch of evenly spaced leucine residues, which is indicative of a zipper motif (amino acids 1041–1104). These observations suggest that Tbc1 regulates gene transcription.

Preparation of Anti-Tbc1 sera: To purify Tbc1, a Tbc-1-glutathione S transferase (GST) fusion protein was produced in *E. coli* from a pGEX3 (Pharmacia) expression plasmid having a BamHI fragment encoding the C-terminal 67 amino acids of Tbc1. The fusion protein was purified on glutathione-sepharose beads using standard protocols. Polyclonal antisera was produced by injection of the purified fusion protein into New Zealand white rabbits (using at least 500 mg of fusion protein at two week intervals). After 6 weeks, serum was tested by Western blot analysis of cell lysates having Tbc1. Antisera was affinity purified using fusion protein coupled to a glutathione-sepharose column. The purified fusion protein and standard techniques can also be used to produce monoclonal antibodies.

Figure 5:
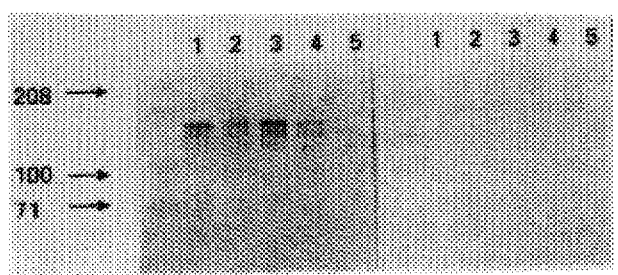
FIG. 5 is a photograph obtained from Western blot analysis of the Tbc1 protein using Tbc1 antisera (left) or preinnnune sera (right). P815 cells (lane 1), PGT6 cells (lane 2), MC8 cells (lane 3), MEL cells (lane 4), and NIH 3T3 cells (lane 5) were used in this assay. The numbers to the left of the photograph indicate approximate molecular weights.
Figure 6A:
FIG. 6A–D is a series of photographs obtained from indirect immunofluorescence of several cell types: (A) MEL cells stained with pre-immune sera, (B) MEL cells stained with Tbc1 antisera, (A) P815 cells stained with Tbc1 antisera, and (D) PGT6 cells stained with Tbc1 antisera.
Figure 6B:
Figure 6C:
Figure 6D:
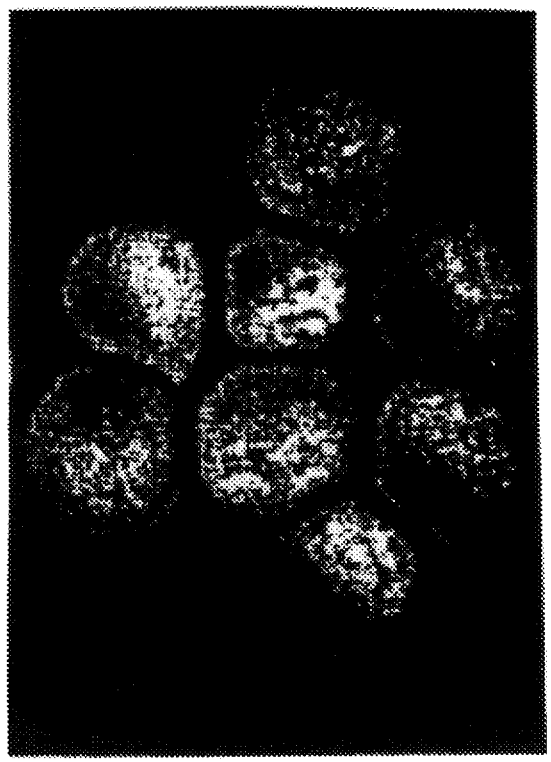

Subcellular localization and cell-specific distribution of Tbc1: Western blot analysis with pre-immune sera demonstrated no specific bands (FIG. 5, right); Tbc1 antisera detected the native Tbc1 protein as a doublet of 140–160 kD in P815, PGT6, and MEL cells (FIG. 5, left). The antisera detected one band in Western blot analysis of NIH 3T3 cells. These results are in accordance with the single band found in Northern blot analysis of NIH 3T3 and the two bands found in Northern blot analysis of P815, PGT6, and MEL cells (FIG. 4).

Immunofluorescence: Indirect immunofluorescence was performed as described previously on cells which were spun onto glass coverslips at 400 rpm in a cytospin (Shandon). Cells were fixed in 100% methanol at −20° C. for 10 minutes, and then washed five times in a solution of phosphate buffered saline (PBS) and 3% fetal calf serum. The cells were then incubated at 37° C. for 45 minutes in a 1:40–1:100 dilution of primary antibody. Cells were washed five times in PBS/serum and incubated with fluorescein-conjugated anti-rabbit serum (1:1000 dilution) for 45 minutes at 37° C. Cells were washed an additional five times in PBS/serum, mounted on glass slides, and visualized by UV microscopy.

FIG. 6 is series of photographs obtained by indirect immunofluorescence which show that the protein is localized in the nucleus in MEL (FIG. 6B), P815 (FIG. 6C), and PGT6 (FIG. 6D) cells. Almost all cells showed some degree of staining of the nucleus, however, cells that were undergoing mitosis (such as in FIG. 6B) did not show evidence of staining. Western blot analysis of human T-cells collected at different stages of the cell cycle indicated that there is approximately the same amount of protein in cells at G0 and $G_2$. Thus, the lack of staining in mitotic cells is likely to reflect Tbc1 protein diffusion into the cytoplasm.

Immunoperoxidase staining: Immunoperoxidase staining of mouse tissues revealed a diverse pattern of expression (FIG. 7). Cryostat sections or samples on glass coverslips were fixed in fresh 2% buffered paraformaldehyde for five minutes and immersed in 100% methanol for five minutes. Immunolabelling was achieved with a 3-layer peroxidase-anti-peroxidase method. The first layer included anti-Tbc-1 primary antibody or preimmune serum (a control); the second layer included goat anti-rabbit IgG (1:50 dilution); and the third layer included rabbit anti-peroxidase-peroxidase complex (1:100 dilution) solution. All incubations were for 1 hour, and the samples were washed 4 times with PBS-0.2% gelatin. A DAB-hydrogen peroxide solution containing 0.3% azide (to block endogenous mammalian peroxidases) was used to localize antibody deposition. Slides were counterstained with hematoxylin, dehydrated, and mounted for microscopic examination.

Figure 7A:
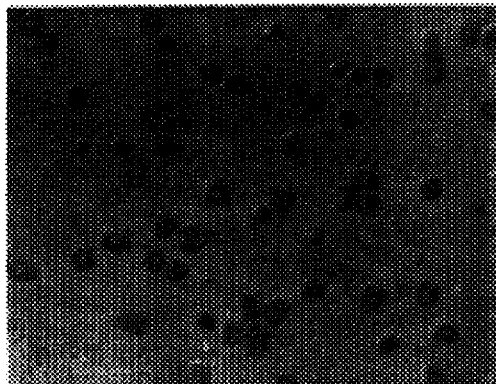
FIG. 7A–F is a series of photographs obtained from immunoperoxidase staining of murine hematopoietic sites and testis with Tbc1 antisera. (A) bone marrow stained with pre-immune sera; (B) bone marrow stained with Tbc1 antisera erythroblasts (straight arrow) and megakaryocytes (open curved arrow) demonstrate intense nuclear staining, but neutrophils (closed curved arrow) do not express appreciable levels of Tbc1; (C) spleen: arrows point to erythroid cluster expressing Tbc1; (D) testicular tissue stained with preimmune sera; (E) testicular tissue stained with Tbc1 antisera; (F) testicular tissue stained with Tbc1 antisera at high magnification; primordial germ cells (closed arrow), primary and secondary spermatocytes (open arrow).
Figure 7D:
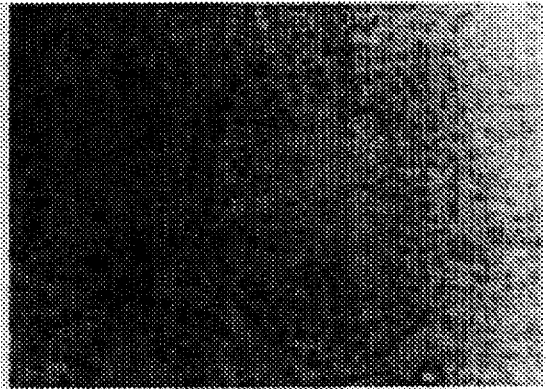
Figure 7B:
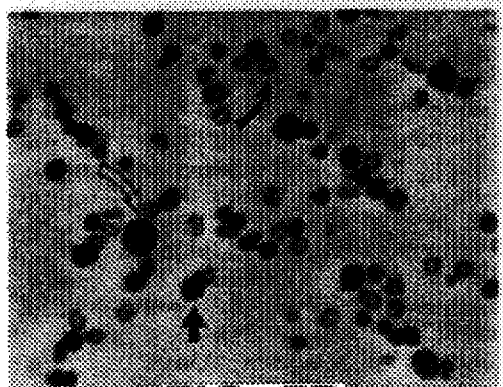
Figure 7E:
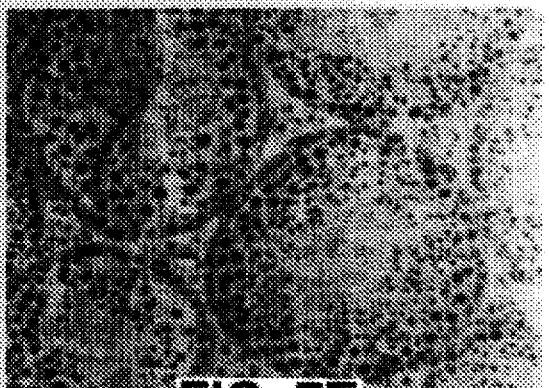
Figure 7C:
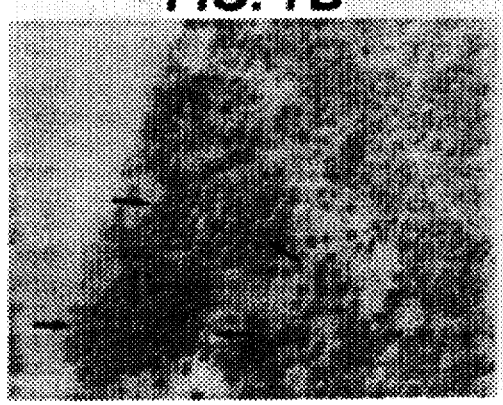
Figure 7F:
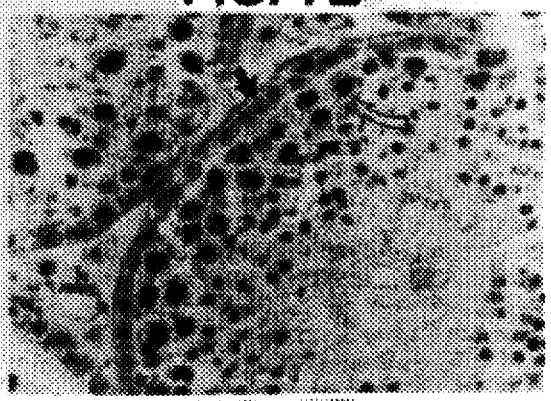

Immunoperoxidase staining of murine bone marrow demonstrated that erythroid cells (FIG. 7B, straight arrow) and megakaryocytes (open arrow) expressed substantial levels of Tbc1 protein in the nucleus, but none was detected in mature neutrophils (curved closed arrow). Bone marrow-derived mast cells also had significant levels of Tbc1 protein (data not shown). Erythroid foci in the spleen expressed abundant Tbc1 (FIG. 7C). The pattern of expression is very similar to the hematopoietic cellular distribution of GATA-1 or GATA-2, suggesting that Tbc1 is a direct target of the GATA-binding proteins.

Primordial spermatogonia of healthy males (FIG. 7F, closed arrow) did not express appreciable levels of Tbc1. However, Tbc1 was abundant in primary and secondary spermatocytes (open arrow). More mature spermatozoa exhibited decreased expression relative to spermatocytes. Leydig cells, myoepithelial cells, and Sertoli cells of the testis expressed low levels of Tbc1.

Chromosomal localization of murine and human Tbc1: A panel of DNAs from AKXD and BXD recombinant inbred (RI) lines was used to map the murine locus for the Tbc1 protein (All mice strains were obtained from The Jackson Laboratory (Bar Harbor, Me.)). Genomic DNA (approximately 5 μg/sample) for the $C57BL_6J$, AKR/J, and DBA/2J progenitors of the AKXD and BXD RI lines were digested with 28 different restriction enzymes. Southern blot analysis was carried out using standard techniques. For the ApaI digests, agarose gel electrophoresis was performed in a 0.8% agarose gel and DNA was electrophoresed for 24 hours at 40 volts in a medium IBI gel apparatus (IBI model MPH). Southern blots were probed with a 850 bp Tbc1 cDNA fragment, and restriction fragment length polymorphisms (RFLPs) were identified.

The presence of 19.5 kb and 12.8 kb genomic DNA bands in AKR/J or a 12.8 kb fragment in DBA/2J indicated the presence of an EcoRI RFLP for Tbc1. This EcoRI allele was characterized for 24 DNAs from the AKXD DNA panel. The strain distribution patterns of Tbc1 and the locus encoding phosphoglucomutase, Pgm-1, indicated close linkage of these two loci on chromosome 5. Perfect concordance was observed with the AKXD strain distribution pattern for the Pgm-1 and Tbc1 loci, indicating linkage with less than one map unit distance from Tbc1 to Pgm-1 (x1).

The presence of 10.0 kb and 4.0 kb genomic DNA bands in C57BL/6J or 12.3 kb and 4.0 kb bands in DBA/2J indicates an ApaI RFLP for Tbc1. This ApaI allele was characterized for 26 DNAs from the BXD DNA panel. The strain distribution patterns for Tbc1 and Pgm-1 indicate close linkage of these two loci on Chromosome 5. Perfect concordance was observed with the BXD distribution pattern for the Pgm-1 and Tbc1 loci, indicating linkage of less than one map unit distance from Tbc1 to Pgm-1 (x1).

Use of Tbc1 to Treat Leukemia

The pattern of Tbc1 expression and its relationship to cell cycle regulators indicate that, in the maturation of mast cells, Tbc1 functions to delay the cell cycle and induce cell-specific transcription which leads to cell differentiation. Tbc1, when expressed in leukemic stem cells, can be used to induce cellular differentiation, pushing the cell out of its leukemic phase. Thus, Tbc1 provides a useful therapeutic for leukemia in a patient. Subtypes of leukemias which can be treated with the method are those which are characterized by an excessive proliferation of hematopoietic cells in which Tbc1 is not expressed. Such subtypes include the $M_1$, $M_2$, $M_3$, $M_4$, $M_5$, $L_1$, $L_2$, or $L_3$ leukemias. The leukemic stem cell can be a pluripotent stem cell or a stem cell of myeloid or lymphoid lineage. Standard techniques can be used for isolation and identification of such cells (Spangrude et al., 1991, Blood, 78: 1395–1402).

Expression of Tbc1 in a leukemic stem cell(s) can be accomplished by transducing the stem cell with a retrovirus or adenovirus into which the Tbc1 gene has been cloned. Appropriate retroviral and adenoviral vectors include adeno-associated viruses and Moloney viruses. Now that the Tbc1 gene has been cloned and sequenced, subcloning the Tbc1 gene into a retroviral vector for expression in a pluripotent stem cell is well within the realm of any skilled molecular biologist employing standard methods.

For expression of Tbc1 in a leukemic stem cell of a patient (e.g., a human), bone marrow is isolated from the patient using standard techniques such as aspiration or needle biopsy. The leukemic stem cell then is transduced with a retrovirus carrying the Tbc1 gene. Delivery of Tbc1 to a cell and its expression can be monitored by analyzing extracts of the transduced cell for Tbc1 RNA, DNA, or protein. This analysis can include techniques such as Northern, Southern, or Western blotting; slot or dot blot assays; radioimmune assays; ELISAs; fluorescent immunoassays; in situ hybridization; PCR amplification of nucleic acids; and/or immunoprecipitation. Examples of suitable methods for detecting Tbc1 in cells are described in detail above. Following transduction of the Tbc1 gene into the stem cell, the cell can be returned to the patient by techniques which are commonly used for bone marrow engraftment (see, e.g., Bodine et al., 1994, Blood 84:1482–1491). Expression of Tbc1 in vivo can later be confirmed by detection of Tbc1 RNA or protein in bone marrow obtained from the patient. Expression of Tbc1 in a leukemic stem cell can be used in combination, or in sequence, with any of several known leukemia therapies. For example, a patient can be treated with Tbc1 therapy and chemotherapy.

Use of Tbc1 to Diagnose $M_6$ and $M_7$ Leukemias

I have found that Tbc1 is expressed in erythrocytes and megakaryocytes, and thus methods for detecting Tbc1 expression are useful in diagnosing leukemias of erythrocytes (e.g., $M_6$) and megakaryocytes (e.g., $M_7$). Because Tbc1 is a marker of erythrocytes and megakaryocytes, anti-Tbc1 antibodies can be used in the same manner as other antibodies (e.g., anti-platelet GPIIb/IIIa, anti-platelet GPIb, and anti-CD10) are used for immunophenotyping leukemia. In diagnosing the leukemia, standard techniques are used to isolate a bone marrow sample or peripheral blood sample from a patient (e.g., a human) suspected of having leukemia. The sample is then analyzed for extensive proliferation (e.g., a white blood count of more than $1 \times 10^5$ cells per μL) of erythrocytes or megakaryocytes. In addition, anti-Tbc1 antibodies or probes can be used in conjunction with previously-described methods for diagnosing leukemia.

Erythrocytes and megakaryocytes can be identified by their immunoreactivity with anti-Tbc1 antibodies. The methods described above for immunofluorescence and immunostaining provide examples of how anti-Tbc1 antibodies can be used to detect erythrocytes and megakaryocytes. Erythrocytes and megakaryocytes can be distinguished from each other on the basis of cell size and/or immunoreactivity to cell-specific antibodies (e.g., anti-platelet GPIb). In addition, probes which hybridize to Tbc1 RNA can be used to detect erythrocytes and megakaryocytes in bone marrow or peripheral blood samples of the patient. Appropriate methods include in situ hybridizations, RT-PCR, RNase protection assays, FACS analysis, and Northern analysis.

Use of Tbc1 to Diagnose Spermatogenesis Disorders

I have also found that Tbc1 is a biochemical marker for primary and secondary spermatocytes. Methods which detect the presence of Tbc1 in testicular tissue can be used to diagnose spermatogenesis disorders. The spermatogenesis disorders Testicular Maturation Arrest (TMA) and azoospermia are characterized by the inability of the male to produce appreciable levels of spermatozoa in seminal fluid. TMA is further characterized by the production of primary and secondary spermatocytes in testicular tissue. In contrast, azoospermia is characterized by the failure to produce primary or secondary spermatocytes. Thus, the presence of primary or secondary spermatocytes in testicular tissue, and a low count of spermatozoa in seminal fluid is indicative of TMA.

The absence of Tbc1 in testicular tissue signifies an abnormality in spermatogenesis. The defect can result in the production of mutant primary or secondary spermatocytes or the complete absence of primary and secondary spermatocytes (azoospermia). The presence of normal levels of Tbc1 in testicular tissue of males who lack mature spermatozoa indicates that the defect results in an arrest of spermatogenesis after the development of primary and secondary spermatocytes (e.g., in the transition from secondary spermatocytes to spermatids or spermatids to spermatozoa). The use of Tbc1 levels in the diagnosis of spermatogenesis disorders provides a means for distinguishing various causes of infertility.

To detect primary and secondary spermatocytes, testicular tissue is assayed for expression of Tbc1 as described above. For example, using the guidance provided herein and methods which are known in the art, anti-Tbc1 antibodies can be used to assay for normal primary and secondary spermatocytes. Tbc1 levels can also be measured by assaying for Tbc1 RNA. Appropriate methods include FACS analysis and RNA hybridization techniques, such as in situ hybridization. The normal levels of Tbc1 in those cells can readily be determined by a comparative analysis of tissue obtained from healthy males. A relatively low level of Tbc1 is indicative of a block in the formation of normal spermatocytes. A normal level of Tbc1 is indicative of the presence of normal spermatocytes and arrest at the late stages of spermatogenesis.

What is claimed is:

1. A substantially pure DNA encoding a Tbc1 polypeptide having an amino acid sequence as set forth in SEQ ID No. 2.

2. The DNA of claim 1, wherein said DNA has 80% or greater sequence identity to the DNA sequence of FIG. 1 (SEQ ID No. 1).

3. The DNA of claim 2, wherein said DNA is the DNA of FIG. 1 (SEQ ID No. 1).

* * * * *